United States Patent [19]

Tanaka et al.

[11] Patent Number: 4,564,619

[45] Date of Patent: Jan. 14, 1986

[54] CARBOSTYRIL DERIVATIVE

[75] Inventors: Tatsuyoshi Tanaka, Sapporo; Kazuyoshi Nagami; Shigeharu Tamada, both of Tokushima; Kazuyuki Nakagawa, Tokushima, all of Japan

[73] Assignee: Otsuka Pharmaceutical Co., Ltd., Japan

[21] Appl. No.: 528,887

[22] Filed: Sep. 2, 1983

[30] Foreign Application Priority Data

Sep. 3, 1982 [JP] Japan .................... 57-154090
Dec. 3, 1982 [JP] Japan .................... 57-213167
Jun. 24, 1983 [JP] Japan .................... 58-114679

[51] Int. Cl.$^4$ .................... C07D 215/22; A61K 31/47
[52] U.S. Cl. .................... 514/312; 546/155; 546/157; 546/158
[58] Field of Search .................... 546/157, 158, 155; 424/258; 514/312

[56] References Cited

U.S. PATENT DOCUMENTS

| | | | |
|---|---|---|---|
| 4,044,141 | 8/1977 | Bossert et al. | 546/257 |
| 4,081,447 | 3/1978 | Prasad et al. | 546/158 |
| 4,288,452 | 9/1981 | Sombroek et al. | 546/158 |
| 4,298,739 | 11/1981 | Nishi et al. | 546/158 |
| 4,450,165 | 5/1984 | Araki et al. | 546/158 |
| 4,482,560 | 11/1984 | Banno et al. | 546/158 |

FOREIGN PATENT DOCUMENTS

| | | | |
|---|---|---|---|
| 90270 | 8/1978 | Japan | 546/157 |
| 87368 | 8/1978 | Japan | 546/157 |

OTHER PUBLICATIONS

Nishi, T. et al., Chem. Abstracts 90:38801h (JA 78/90270).
Nishi, T. et al., Chem. Abstracts 90:38802j (JA 78/87363).

Primary Examiner—George F. Lesmes
Assistant Examiner—S. A. Gibson
Attorney, Agent, or Firm—Finnegan, Henderson, Farabow, Garrett & Dunner

[57] ABSTRACT

Carbostyril derivative or a pharmaceutically acceptable acid addition salt thereof, having excellent platelate aggregation inhibitory effect, calcium antagonism, hypotensive effect and phosphodiesterase inhibitory effect are useful as prophylactic or treating agents for thrombosis, circulation improving agents for coronary blood flow such as coronary vasodilators, hypotensive agents and phosphodiesterase inhibitors. Furthermore, the carbostyril derivatives are weak in heart rate increasing activity and also in cardiac muscle contraction increasing activity, and the carbostyril derivatives are useful agents for curing and treating heart diseases such as cardiac angina and myocardial infarction caused by hypercoagulability of the platelets. Processes are disclosed for preparation of the carbostyril derivatives.

26 Claims, 11 Drawing Figures

CARBOSTYRIL DERIVATIVE

The present invention relates to a novel carbostyril derivative and its salts, having excellent platelet aggregation inhibitory effect, calcium antagonism, hypotensive effect and phosphodiesterase inhibitory effect, processes for preparing the same and a pharmaceutical composition containing the same as the active ingredient.

The carbostyril derivative of the present invention is novel and has not been known in any literature and is represented by the general formula (1) as follows:

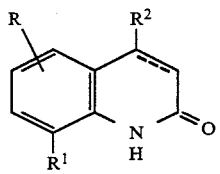

[where R is a hydrogen atom or a group of the formula

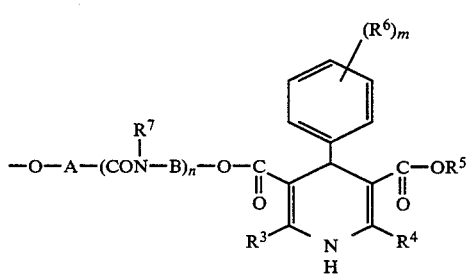

(wherein $R^3$, $R^4$ and $R^5$ are each a lower alkyl group; A is a lower alkylene group which may have a hydroxyl group or a lower alkanoyloxy group as the substituent; $R^6$ is a nitro group, a lower alkyl group which may have halogen atoms as the substituent, a halogen atom, a lower alkoxy group, a lower alkylthio group, a lower alkoxycarbonyl group; $R^7$ is a lower alkyl group or a cycloalkyl group; B is a lower alkylene group; n is 0 or 1; and m is 0 or an integer of 1, 2 or 3); $R^1$ is a hydrogen atom, a hydroxyl group, a lower alkoxy group, a lower alkenyloxy group, a lower alkynyloxy group, a 2-tetrahydropyranyloxy group or a group of the formula,

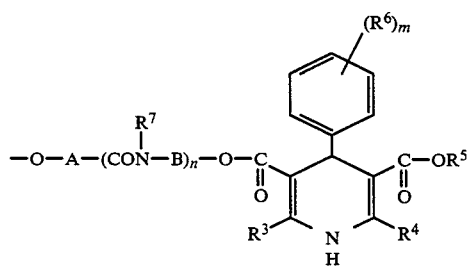

(wherein $R^3$, $R^4$, $R^5$, $R^6$, $R^7$, A, B m and n are the same as defined above); $R^2$ is a hydrogen atom, a lower alkyl group or a group of the formula,

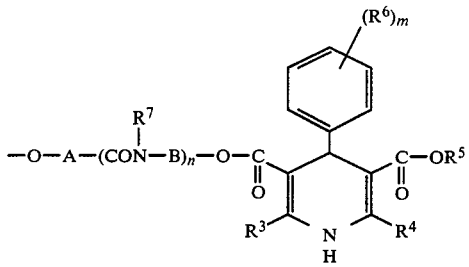

(wherein $R^3$, $R^4$, $R^5$, $R^6$, $R^7$, A, B, m and n are the same as defined above); provided that, among the symbols of R, $R^1$ and $R^2$, the only one of them should be of a group of the formula,

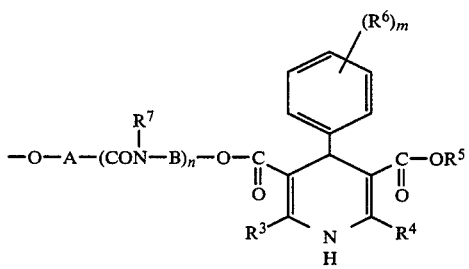

(wherein $R^3$, $R^4$, $R^5$, $R^6$, $R^7$, A, B, m and n are the same as defined above); and the carbon-carbon bond between 3- and 4-positions in the carbostyril skeleton is a single or double bond].

The carbostyril derivative represented by the general formula (1) of the present invention is excellent in platelet aggregation inhibitory effect, calcium antagonism, hypotensive effect; therefore the carbosytril derivative (1) is useful as prophylactic or treating agent for thrombosis, circulation improving agent for coronary blood flow such as coronary vasodilator, hypotensive agent and phosphodiesterase inhibitor.

Specifically, the carbostyril derivative (1) of the present invention is very weak both in the heart rate increasing activity and in the cardiac muscle contraction increasing activity. Furthermore, the carbostyril derivative (1) of the present invention has an excellent absorption property to the living body.

Generally, cardiac angina is a disease which causes myocardial ischemia due to the imbalance of supply and demand (consumption) of oxygen in the cardiac muscles, and myocardial infarction is a disease which causes myocardial ischematic necrosis due to the hematogenic dyscrasis to the cardiac muscles. Thus, in treating and curing cardiac angina and myocardial infarction, the factors for exacerbating heart failure should be eliminated as much as possible, so as to relieve the myocardiac dyscrasia. In this connection, attention should be paid necessarily for decreasing the oxygen demand in the cardiac muscles, as well as for increasing the oxygen supply to the cardiac muscles.

Since, as explained above, the carbostyril derivative (1) of the present invention is very weak in the heart rate increasing activity, and in the cardiac muscle contraction increasing activity, both of which cause an increase of oxygen demand in the cardiac muscles, the carbostyril derivative (1) of the present invention is quite useful as prophylactic or treating agent for curing the heart diseases, for example cardiac angina and myocardial infarction, caused by hypercoagulability of the platelets, as well as being quite useful as a hypotensive agent.

An object of the present invention is to provide a novel carbostyril derivative and its salt, having the above-mentioned excellent pharmacological activities.

Another object of the present invention is to provide processes for preparing said carbostyril derivative.

A further object of the present invention is to provide a pharmaceutical composition containing said carbostyril derivative as the active ingredient.

BRIED DESCRIPTION OF THE DRAWINGS

Figure 1:
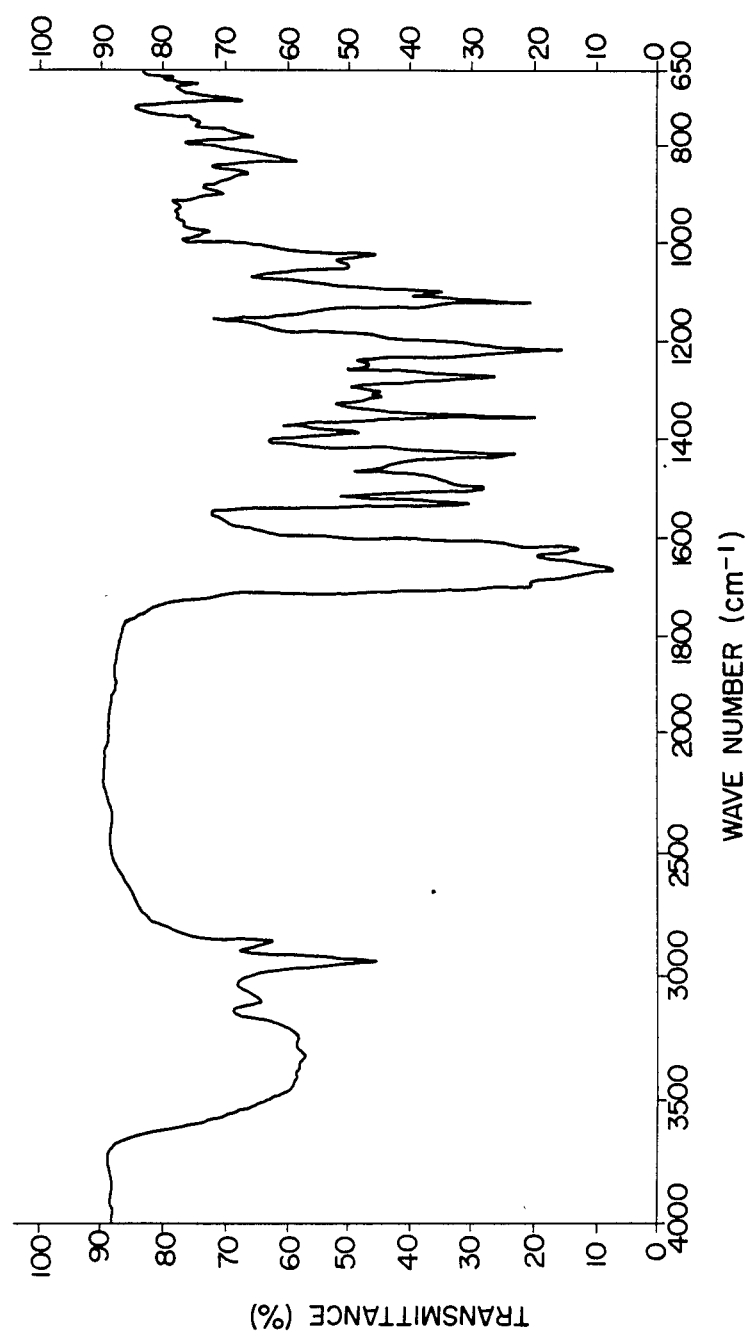
FIG. 1 is an infrared (IR) absorption spectrum of the compound prepared in Example 61.

As to the lower alkyl group which may have halogen atoms as the substituents, an alkyl group having 1 to 6 carbon atoms which may have 1 to 3 halogen atoms as the substituents, such as methyl, ethyl, propyl, isopropyl, butyl, tert-butyl, pentyl, hexyl, trifluoromethyl, 2,2-difluoroethyl, 1,1-dichloroethyl, trichloromethyl, dichloromethyl, tribromomethyl, 2,2,2-trifluoroethyl, 2,2,2-trichloroethyl, 2-chloroethyl, 1,2-dichloroethyl, 3,3,3-trichloropropyl, 3-fluoropropyl, 4-chlorobutyl and 3-chloro-2-methylethyl groups can be exemplified.

As to the lower alkoxy group, an alkoxy group having 1 to 6 carbon atoms such as methoxy, ethoxy, propoxy, isopropoxy, butoxy, tert-butoxy, pentyloxy and hexyloxy groups can be exemplified.

As to the lower alkenyloxy group, an alkenyloxy group having 2 to 6 carbon atoms such as vinyloxy, alloyloxy, 2-butenyloxy, 3-butenyloxy, 1-methylallyloxy, 2-pentenyloxy and 2-hexenyloxy groups can be exemplified.

As to the lower alkynyloxy group, an alkynyloxy group having 2 to 6 carbon atoms such as ethynyloxy, 2-propynyloxy, 2-butynyloxy, 3-butynyloxy, 1-methyl-2-propynyloxy, 2-butynyloxy, 3-butynyloxy, 1-methyl-2-propynyloxy, 2-pentynyloxy, and 2-hexynyloxy groups can be exemplified.

As to the lower alkylene group which may have a hydroxyl group or a lower alkanoyloxy group as the substituent, an alkylene group having 1 to 6 carbon atoms which may have, as the substituent, a hydroxyl group or an alkanoyloxy group having 1 to 6 carbon atoms in the alkyl moiety, such as methylene, ethylene, methylmethylene, trimethylene, 2-methyltrimethylene, 2,2-dimethyltrimethylene, tetramethylene, pentamethylene, hexamethylene, 2-ethyltrimethylene, 1-methyltrimethylene, hydroxymethylene, 1-hydroxyethylene, 1-hydroxymethylmethylene, 3-hydroxytrimethylene, 2-hydroxytrimethylene, 1-hydroxytrimethylene, 3-hydroxy-2-methyltrimethylene, 2,2-dimethyl-1-hydroxytrimethylene, 4-hydroxytetramethylene, 3-hydroxytetramethylene, 3-hydroxypetamethylene, 5-hydroxypentamethylene, 2-hydroxyhexamethylene, 2-ethyl-1-hydroxytrimethylene, 3-hydroxy-1-methyltrimethylene, 4-hydroxyhexamethylene, acetyloxymethylene, 2-acetyloxyethylene, 1-propionyloxyethylene, 1-butyryloxymethylmethylene, 3-pentanoyloxytrimethylene, 2-acetyloxytrimethylene, 1-formyloxytrimethylene, 3-hexanoyloxy-2-methyltrimethylene, 2,2-dimethyl-1-acetyloxytrimethylene, 4-butyryloxytetramethylene, 3-pentanoyloxytetramethylene, 3-acetyloxypentamethylene, 5-hexanoyloxypentamethylene, 2-acetyloxyhexamethylene, 2-ethyl-1-propionyloxytrimethylene, 3-butyryloxy-1-methyltrimethylene and 4-hexanoyloxyhexamethylene groups can be exemplified.

As to the halogen atom, fluorine atom, chlorine atom, bromine atom and iodine atom can be exemplified.

As to the lower alkylthio group, an alkylthio group having 1 to 6 carbon atoms such as methylthio, ethylthio, propylthio, isopropylthio, butylthio, tert-butylthio, pentylthio and hexylthio groups can be exemplified.

As to the lower alkoxycarbonyl group, an alkoxycarbonyl group having 1 to 6 carbon atoms in the alkyl moiety such as methoxycarbonyl, ethoxycarbonyl, propoxycarbonyl, isopropoxycarbonyl, butoxycarbonyl, tert-butoxycarbonyl, pentyloxycarbonyl and hexyloxycarbonyl groups can be exemplified.

As to the lower alkyl group, an alkyl group having 1 to 6 carbon atoms such as methyl, ethyl, propyl, isopropyl, butyl, tert-butyl, pentyl and hexyl groups can be exemplified.

As to the cycloalkyl group, a cycloalkyl group having 3 to 8 carbon atoms such as cyclopropyl, cyclobutyl, cyclopentyl, cyclohexyl, cycloheptyl and cyclooctyl groups can be exemplified.

As to the lower alkyklene group, the alkylene group having 1 to 6 carbon atoms such as methylene, ethylene, methylmethylene, trimethylene, 2-methyltrimethylene, 2,2-dimethyltrimethylene, tetramethylene, pentamethylene, hexamethylene, 2-ethyltrimethylene and 1-methyltrimethylene groups can be exemplified.

The carbostyril derivative represented by the general formula (1) of the present invention can be prepaed by various methods, and examples of preferable processes are shown as follows:

Reaction scheme - 1

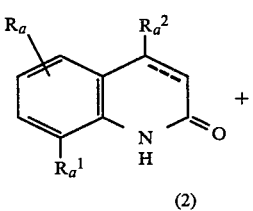

(2)

-continued
Reaction scheme - 1

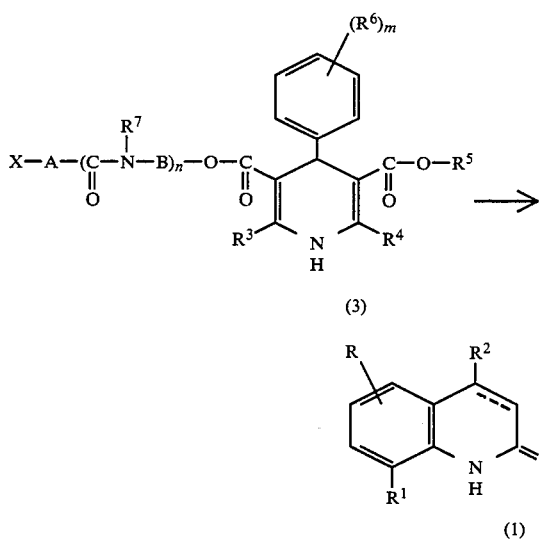

(3)

(1)

[wherein R, $R^1$, $R^2$, $R^3$, $R^4$, $R^5$, $R^6$, $R^7$, A, B, n, m and the carbon-carbon bond between 3- and 4-positions in the carbostyril skeleton are the same as defined above; $R_a$ is a hydrogen atom or a hydroxyl group; $R_a{}^1$ is a hydrogen atom, a hydroxyl group, a lower alkoxy group, a lower alkenyloxy group, a lower alkynyloxy group or a 2-tetrahydropyranyloxy group; $R_a{}^2$ is a hydrogen atom, a hydroxyl group or a lower alkyl group; X is a halogen atom; provided that, among R, $R^1$ and $R^2$, only one of them should be a group of the formula,

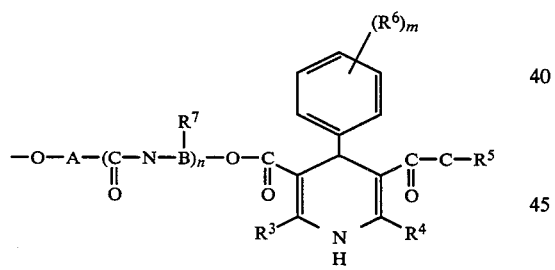

(wherein $R^3$, $R^4$, $R^5$, $R^6$, $R^7$, A, B, m and n are the same as defined above)].

Thus a carbostyril derivative represented by the general formula (1) can be prepared by reacting a hydroxycarbostyril derivative represented by the general formula (2) with a compound represented by the general formula (3) under dehydrohalogenating reaction conditions. The dehydrohalogenating reaction is carried out in the presence of a basic compound as the dehydrohalogenating agent. As to the basic compound, any basic compound known in the art can be used, for example an inorganic basic compound such as sodium hydroxide, potassium hydroxide, sodium carbonate, potassium carbonate, sodium hydrogencarbonate, potassium hydrogencarbonate, or silver carbonate; an alcoholate such as sodium methylate or sodium ethylate, an organic basic compound such as triethylamine, pyridine or N,N-dimethylaniline are exemplified.

The dehydrohalogenating reaction can be carried out in the presence of a solvent, and as to the solvent, any inert solvent which does not give any adverse effect to the reaction can be used, for example, alcohols such as methanol, ethanol, propanol, butanol and ethylene glycol; ethers such as dimethyl ether, tetrahydrofuran, dioxane, monoglyme and diglyme; ketones such as acetone and methyl ethyl ketone; atomatic hydrocarbons such as benzene, toluene and xylene; esters such as methyl acetate and ethyl acetate; and aprotic polar solvents such as N,N-dimethylformamide, dimethyl sulfoxide and hexamethylphosphoryl triamide can be exemplified.

The dehydrohalogenating reaction can be also carried out in the presence of a metal iodide for example sodium iodide or potassium iodide.

The ratio of the amount of the compound (2) to the amount of the compound (3) is not specifically restricted and can be selected from a wide range, and generally an equimolar quantity to 5 times the molar quantities, preferably an equimolar quantity to 2 times the molar quantities of the latter is used to the former.

The reaction temperature is also not specifically restricted, and generally the reaction can be carried out at a room temperature to 200° C., preferably from 50° to 160° C.

The reaction is generally carried out for 1 to 30 hours, preferably for 2 to 10 hours.

Reaction scheme - 2

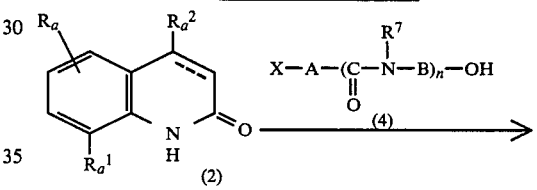

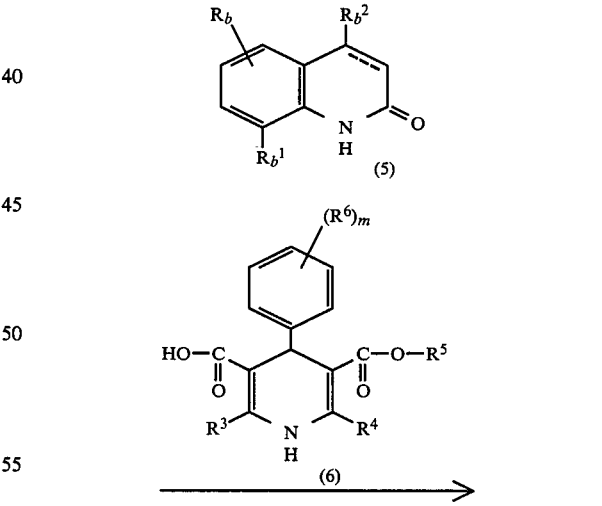

(1)

[wherein R, $R^1$, $R^2$, $R_a$, $R_a{}^1$, $R^2$, $R^3$, $R^4$, $R^5$, $R^6$, $R^7$, A, B, m, n, X and the carbon-carbon bond between 3- and 4-positions in the carbostyril skeleton are the same as defined above; $R_b$ is a hydrogen atom or a group of the formula,

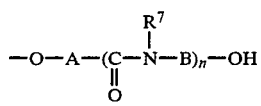

(wherein $R^7$, A, B and n are the same as defined above); $R_b^1$ is a hydrogen atom, a hydroxyl group, a lower alkoxy group, a lower alkenyloxy group, a lower alkynyloxy group, a 2-tetrahydropyranyloxy group or a group of the formula,

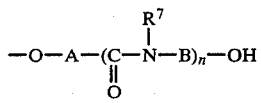

(wherein $R^7$, A, B and n are the same as defined above); $R_b^2$ is a hydrogen atom, a lower alkyl group or a group of the formula,

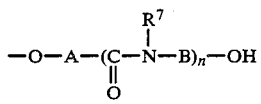

(wherein $R^7$, A, B and n are the same as defined above); provided that, among R, $R^1$ and $R^2$, only one of them should be a group of the formula,

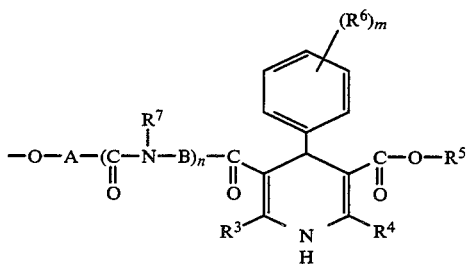

(wherein $R^3$, $R^4$, $R^5$, $R^6$, $R^7$, A, B, m and n are the same as defined above); similarly, among $R_b$, $R_b^1$ and $R_b^2$, only one of them should be a group of the formula,

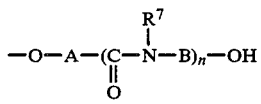

(wherein $R^7$, A, B and n are the same as defined above)].

In the above-mentioned Reaction scheme—2, the reaction of a hydroxycarbostyril derivatives (2) with a compound (4) can be carried out under a reaction condition similar to that of a compound (2) with a compound (3) in the Reaction scheme—1.

The reaction of a compound (5) with a compound (6) is carried out under conventional esterification reaction conditions. This reaction is carried out in the presence of a catalyst, and as to the catalyst, any catalyst widely used in a conventional esterification may be used. Typical examples of the catalysts are inorganic acids such as hydrochloric acid gas, concentrated sulfuric acid, phosphoric acid, polyphosphoric acid, boron trifluoride and perchloric acid; organic acids such as trifluoroacetic acid, trifluoromethansulfonic acid, naphthalenesulfonic acid, p-toluenesulfonic acid, benzenesulfonic acid and ethanesulfonic acid; trifluoromethanesulfonic acid anhydride, thionyl chloride, and acetone dimethylacetal. Furthermore, an acidic ion-exchange resin can also be used as the catalyst.

The amount of the catalyst to be used is not specifically restricted, generally an amount of the catalyst used in a conventional esterification reaction is applied.

The reaction can be carried out either in the absence of or in the presence of a solvent. As to the solvent, any solvent commonly used in an esterification reaction can be used effectively, specifically, organic hydrocarbons such as benzene, toluene and xylene; halogenated hydrocarbons such as dichloromethane, dichloroethane, chloroform and carbon tetrachloride; ethers such as diethyl ether, tetrahydrofuran, dioxane and ethylene glycol monomethyl ether are exemplified.

In the above-mentioned reaction, the ratio of the amount of a compound (5) to the amount of a compound (6) can be selected from a wide range, and in order to obtain the desired product of the present invention in good yield, generally a large excess amount of the latter is used to the former in the absence of a solvent, alternatively, in the presence of a solvent, the latter is used in an equimolar quantity to 5 times the molar quantities, preferably an equimolar quantity to 2 times the molar quantity of the former. Additionally, the yield of the desired product can be increased by removing the water formed in the reaction system by using a dehydrating agent such as anhydrous calcium chloride, anhydrous cupric sulfate, anhydrous calcium sulfate or phosphorus pentoxide.

The reaction temperature is not specifically restricted, and can be selected from a wide range; generally, the reaction can be carried out in the range of from $-20°$ to $200°$ C., preferably from about $0°$ C. to $150°$ C.

The reaction time is dependent on the type of the raw material, and the reaction conditions employed, and generally the reaction is completed in about 10 minutes to 20 hours.

Reaction scheme - 3

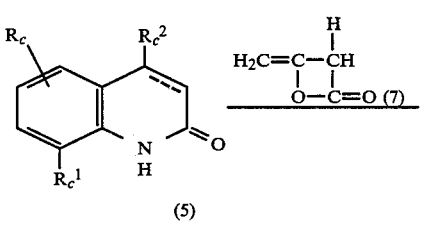

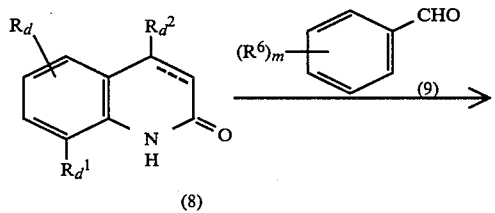

-continued
Reaction scheme - 3

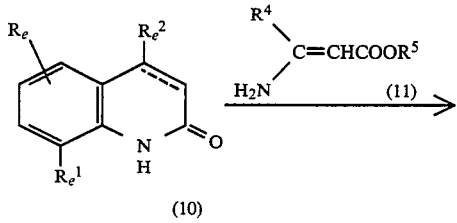

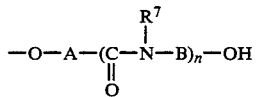

[wherein $R_c$ is a hydrogen atom or a group of the formula,

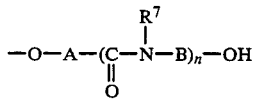

(wherein $R^7$, A, B and n are the same as defined above); $R_c^1$ is a hydrogen atom, a hydroxyl group, a lower alkoxy group, a lower alkenyloxy group, a lower alkynyloxy group, a 2-tetrahydropyranyloxy group or a group of the formula,

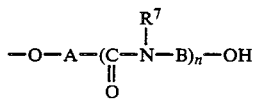

(wherein $R^7$, A, B and n are the same as defined above); $R_c^2$ is a hydrogen atom, a lower alkyl group or a group of the formula,

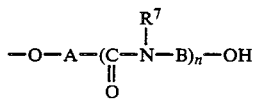

(wherein $R^7$, A, B and n are the same as defined above); $R_d$ is a hydrogen atom or a group of the formula,

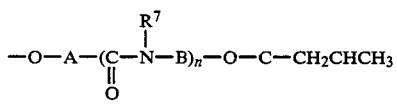

(wherein $R^7$, A, B and n are the same as defined above); $R_d^1$ is a hydrogen atom, a hydroxyl group, a lower alkoxy group, a lower alkenyloxy group, a lower alkynyloxy group, a 2-tetrahydropyranyloxy group or a group or a group of the formula,

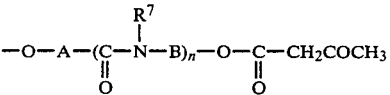

(wherein $R^7$, A, B and n are the same as defined above); $R_d^2$ is a hydrogen atom, a lower alkyl group or a group of the formula,

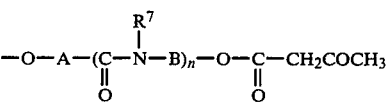

(wherein $R^7$, A, B and n are the same as defined above); $R_e$ is a hydrogen atom or a group of the formula,

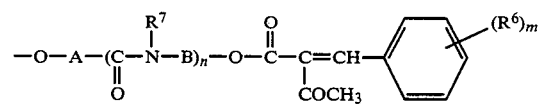

(wherein $R^6$, $R^7$, A, B, m and n are the same as defined above); $R_e^1$ is a hydrogen atom, a hydroxyl group, a lower alkoxy group, a lower alkenyloxy group, a lower alkynyloxy group, a 2-tetrahydropyranyloxy group or a group of the formula,

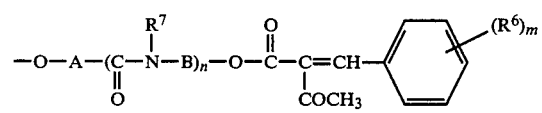

(wherein $R^6$, $R^7$, A, B, m and n are the same as defined above); $R_e^2$ is a hydrogen atom, a lower alkyl group or a group of the formula,

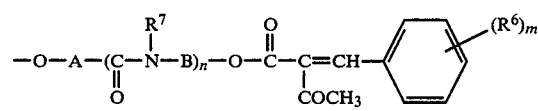

(wherein $R^6$, $R^7$, A, B, m and n are the same as defined above; $R_f$ is a hydrogen atom or a group of the formula,

(wherein $R^4$, $R^5$, $R^6$, $R^7$, A, B, m and n are the same as defined above); $R_f^1$ is a hydrogen atom, a hydroxyl group, a lower alkoxy group, a lower alkenyloxy group, a lower alkynyloxy group, a 2-tetrahydropyranyloxy group or a group of the formula,

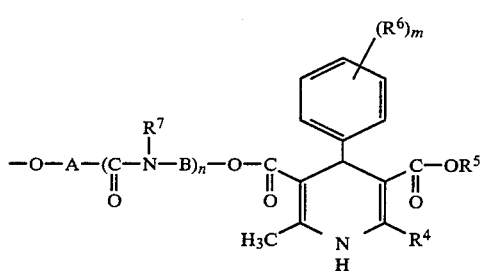

(wherein $R^4$, $R^5$, $R^6$, $R^7$, A, B, m and n are the same as defined above); $R_f^2$ is a hydrogen atom, a lower alkyl group or a group of the formula,

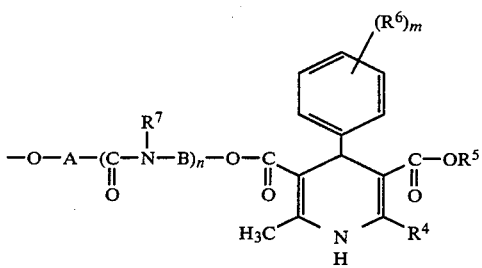

(wherein $R^4$, $R^5$, $R^6$, $R^7$, A, B, m and n are the same as defined above); provided that, among $R_c$, $R_c^1$ and $R_c^2$, only one of them should be a group of the formula,

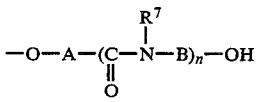

(wherein $R^7$, A, B and n are the same as defined above); among $R_d$, $R_d^1$ and $R_d^2$, only one of them should be a group of the formula,

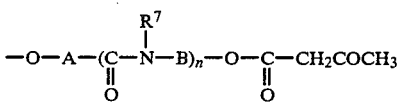

(wherein $R^7$, A, B, and n are the same as defined above); among $R_e$, $R_e^1$ and $R_e^2$, only one of them should be a group of the formula,

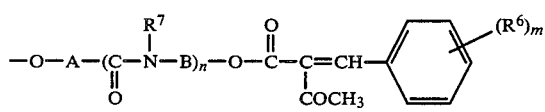

(wherein $R^6$, $R^7$, A, B, m and n are the same as defined above); and among $R_f$, $R_f^1$ and $R_f^2$, only one of them should be a group of the formula,

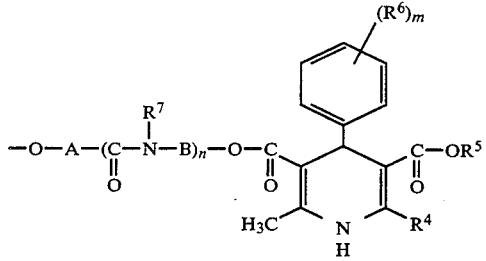

(wherein $R^4$, $R^5$, $R^6$, $R^7$, A, B, m and n are the same as defined above)].

In the Reaction scheme—3 as mentioned above, the reaction of a compound (5) with a compound (7) is carried out in a suitable solvent in the presence of a catalyst. As to the catalyst, the examples include basic compounds such as organic bases, for example triethylamine, pyridine and N,N-dimethylaniline; inorganic bases, for example sodium acetate and potassium carbonate; and acidic compounds such as sulfonic acids, for example p-toluenesulfonic acid, and Lewis acids, for example boron trifluoride. As to the solvent, the examples include aromatic hydrocarbons such as benzene, toluene and xylene; esters such as methyl acetate and ethyl acetate; halogenated hydrocarbons such as methylene chloride, chloroform and 1,2-dichloroethane; ethers such as diethyl ether, tetrahydrofuran, dioxane, monoglyme and diglyme; ketones such as acetone and methyl ethyl ketone; and aprotic polar solvents such as N,N-dimethylformamide, eimethyl sulfoxide, hexamethylphosphoryl triamide and N-methylpyrrolidone.

The ratio of the amount of compound (5) to the amount of compound (7) is generally at least an equimolar quantity, preferably 1 to 2 times the molar quantities of the latter to the former.

The amount of the catalyst is not specifically restricted, and generally 1/100 to 10 times the molar quantities, preferably 1/10 to 5 times the molar quantities of the catalyst to the compound (5) is used.

The reaction is generally carried out at $-20°$ to 200° C., preferably at $-20°$ to 100° C., and is completed generally in 10 minutes to 20 hours.

The reaction of compound (8) thus prepared with compound (9) is also carried out in a suitable solvent in the absence or presence of a catalyst. The examples of solvents include alcohols such as methanol, ethanol, propanol, isopropanol, butanol and ethylene glycol; ethers such as diethyl ether, tetrahydrofuran, dioxane, monoglyme and diglyme; aromatic hydrocarbons such as benzene, toluene and xylene; halogenated hydrocarbons such as methylene chloride, chloroform and 1,2-dichloroethane; aprotic polar solvents such as N,N-dimethylformamide, dimethyl sulfoxide, and hexamethylphosphoryl triamide; carboxylic acids such as acetic acid and propionic acid; and pyridine. The examples of the catalysts include organic bases such as pyridine, piperidine, triethylamine, diethylamine and 1,5-diazabicyclo[5,4,0]undecene-5 (DBU); metal alcoholates such as sodium ethylate and sodium methylate; inorganic bases such as sodium hydroxide, potassium hydroxide, potassium carbonate and potassium acetate; mineral acids such as hydrochloric acid and sulfuric acid; carboxylic acids such as acetic acid and propionic acid; and Lewis acids such as boron trifluoride.

The ratio of the amount of compound (8) to the amount of compound (9) is generally at least an equimolar quantity, preferably an equimolar quantity to 2 times the molar quantities of the latter to the former. The amount of the catalyst is similar to that used in the reaction of compound (5) with compound (7).

The reaction is generally carried out at −20° to 200° C., preferably at −20° to about 150° C., and is completed generally in 10 minutes to 50 hours.

The reaction of compound (10) with compound (11) can advantageously be carried out in the presence of a solvent. As to the solvent, any inert solvent which does not give any adverse effect can be used, and the examples of the solvents include ketones such as acetone; halogenated hydrocarbons such as chloroform; alcohol such as methanol, ethanol, propanol, isopropanol and ethylene glycol; ethers such as diethyl ether, tetrahyrofuran, dioxane, monoglyme and diglyme; aromatic hydrocarbons such as benzene, toluene and xylene; esters such as methyl acetate and ethyl acetate; carboxylic acids such as acetic acid and propionic acid; organic bases such as pyridine; and aprotic polar solvents such as N,N-dimethylformamide, dimethyl sulfoxide and hexamethylphosphoryl triamide.

The ratio of the amount of compound (10) to the amount of compound (11) is generally an equimolar to 10 times, preferably equimolar quantities to 2 times the molar quantity.

The reaction is generally carried out at −20° to 200° C., preferably 50° to 150° C., and generally the reaction is completed in 10 minutes to 20 hours, to obtain a compound represented by the general formula (1a).

The reaction of a compound (8) with a compound (9) can be carried out without separating the intermediate product (10); thus compounds (8), (9) and (11) can be reacted simultaneously in a one pot reaction to obtain the desired product represented by the general formula (1b).

Reaction scheme - 4

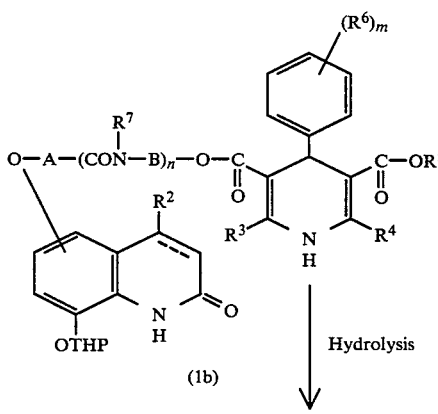

(1b)

Hydrolysis

-continued
Reaction scheme - 4

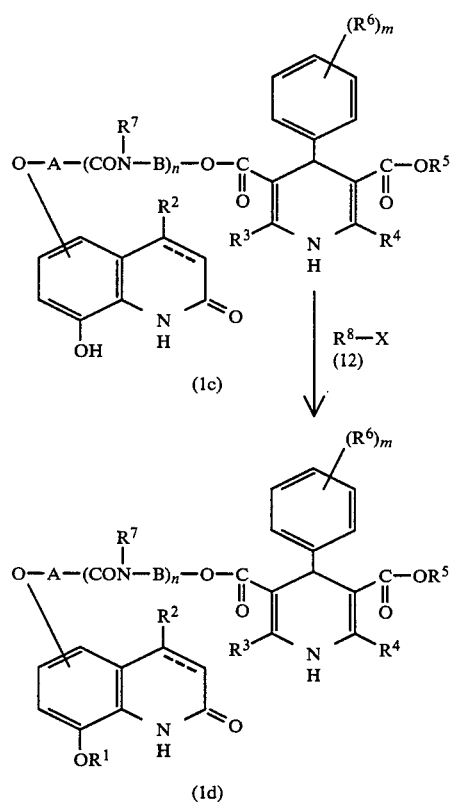

(wherein $R^2$, $R^3$, $R^4$, $R^5$, $R^6$, $R^7$, A, B, m, n, X and the carbon-carbon bond between 3- and 4-positions in the carbostyril skeleton are the same as defined above; $R^8$ is a lower alkyl group, a lower alkenyl group, a lower alkynyl group or a 2-tetrahydropyranyl group; and OTHP is a 2-tetrahydrophyranyloxy group).

According to the above-mentioned Reaction scheme—4, among compounds as represented by the general formula (1), compounds wherein R is a group of the formula,

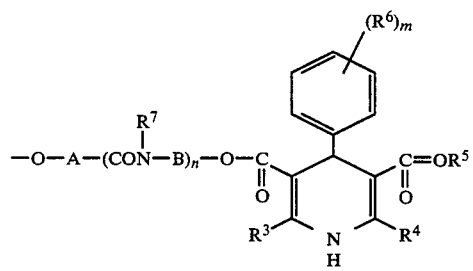

and $R^1$ is a 2-tetrahydropyranyloxy group, i.e., a compound represented by the general formula (1b), can be hydrolyzed to obtain the corresponding compound (i.e., a compound represented by the general formula (1c) wherein $R^1$ is a hydroxyl group; further, a compound (1c) can be reacted with a compound (12) to obtain the corresponding compound, i.e., a compound represented by the general formula (1d), wherein $R^1$ is a lower alkoxy group, a lower alkenyloxy group, a lower alkynyloxy group or a 2-tetrahydropyranyloxy group.

The hydrolysis of a compound (1b) can be carried out in the absence or presence of a suitable solvent with an acid. As to the solvent, water, a lower alcohol such as methanol, ethanol or isopropanol; an ether such as dioxane, or tetrahydrofuran; a ketone such as acetone; acetic acid; or a mixed solvent of these solvents can be exemplified. As to the acid, a mineral acid such as hydrochloric acid or sulfuric acid; a p-toluenesulfonic acid such as pyridine p-toluenesulfonate; or a carboxylic acid such as acetic acid or propionic acid can be exemplified.

The ratio of the amount of the acid is at least an equimolar quantity; generally a large excess quantity of acid can be used relative to the amount of a compound (1b). The reaction temperature is generally $-20°$ to $200°$ C., preferably $-20°$ to $50°$ C., and the reaction is completed generally in 0.5 to 5 hours.

The reaction of a compound (1c) thus obtained with a compound (12) can be carried out under the condition of a conventional alkylating reaction, for example the reaction is carried out in the presence of a basic compound. As to the basic compound to be used in this reaction, an alkali metal such as sodium metal or potassium metal; a hydroxide, a carbonate, a hydrogencarbonate or alcoholate of said alkali metal; an aromatic amine such as pyridine or piperidine; and an organic basic compound such as triethylamine, or 1,8-diazabicycloundecene-7 can be exemplified. The reaction can advantageously proceed in a suitable solvent. As to the solvent used, water; a lower alcohol such as methanol, ethanol, isopropanol or n-butanol; a ketone such as acetone or methyl ethyl ketone; a halogenated hydrocarbon such as chloroform or dichloroethane; an aromatic hydrocarbon such as benzene, toluene or xylene; or a protic polar solvent such as N,N-dimethylformamide or dimethyl sulfoxide can be exemplified.

The ratio of the amount of a compound (1c) to the amount of a compound (12) is at least one and preferably ranges from one to two. The reaction temperature is generally $-20°$ to $200°$ C., preferably about $0°$ to $100°$ C. and the reaction is completed generally in 10 minutes to 20 hours.

Among compounds as represented by the general formula (1), those wherein $R^2$ is a group of the formula

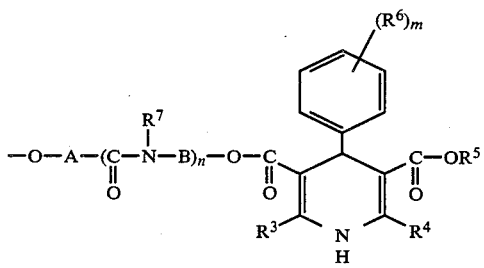

and wherein $R^1$ is a hydroxyl group, a lower alkoxy group, a lower alkenyloxy group, a lower alkynyloxy group or a 2-tetrahydropyranyloxy group can also be converted from the corresponding compound wherein $R^1$ is a 2-tetrahydropyranyloxy group by a method similar to that described in the above-mentioned Reaction scheme—4.

In the above-mentioned Reaction scheme—1, compound (3) wherein n is 0 as used for the starting material can be easily prepared by a method as shown in the following Reaction scheme—5.

Reaction scheme - 5

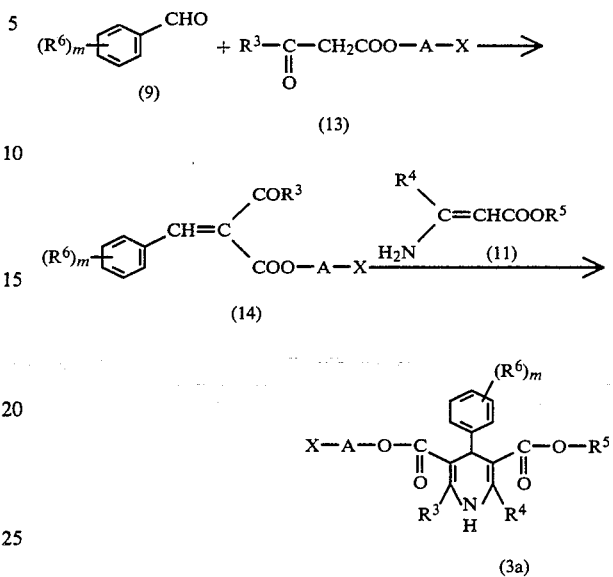

(wherein $R^3$, $R^4$, $R^5$, $R^6$, A, m and X are the same as defined above).

The reaction of a compound (9) with a compound (13) can be carried out under reaction conditions similar to those employed in the reaction of a compound (8) with a compound (9) in the above-mentioned Reaction scheme—3.

The reaction of a compound (14) with a compound (11) can be carried out under reaction conditions similar to those employed in the reaction of a compound (10) with a compound (11) in the above-mentioned Reaction scheme—3.

The reaction of compounds (9), (13) and (11) can be carried out by without separating the intermediate product (14); thus compounds (9), (13) and (11) can be reacted simultaneously in a one pot reaction to obtain the desired product represented by the general formula (3a).

Among carbostyril derivatives represented by the general formula (1), the compounds having a lower alkylene group which may have a hydroxyl group as the substituent can be prepared by a method as shown in the following Reaction scheme—6.

Reaction scheme - 6

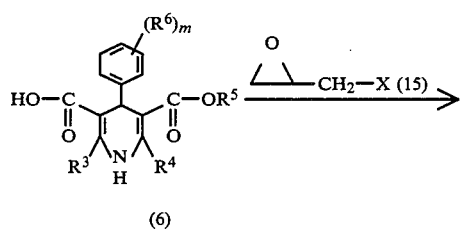

-continued
Reaction scheme - 6

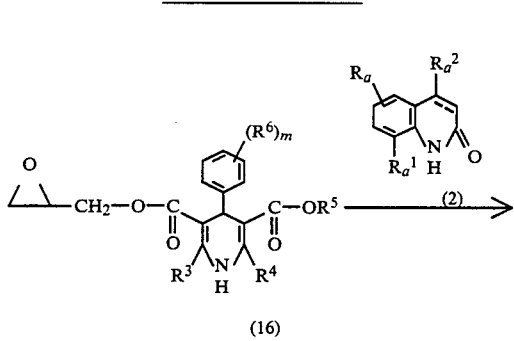

(16)

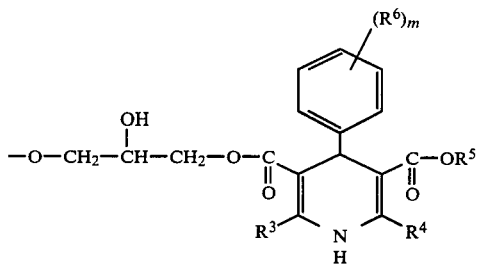

(wherein $R^3$, $R^4$, $R^5$, $R^6$ and m are the same as defined above); $R_h$ is hydrogen atom or a group of the formula,

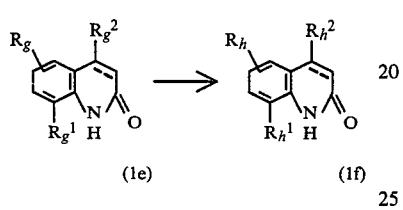

(1e)   (1f)

[wherein $R_a$, $R_a^1$, $R_a^2$, $R^3$, $R^4$, $R^5$, $R^6$, m, X and the carbon-carbon bond between 3- and 4-positions in the carbostyril skeleton are the same as defined above; $R_g$ is a hydrogen atom or a group of the formula,

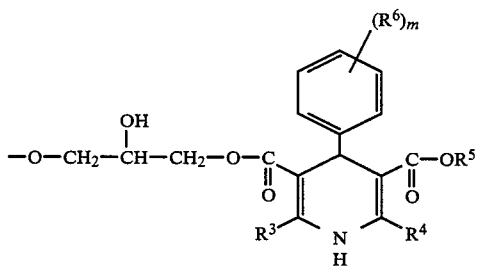

(wherein $R^3$, $R^4$, $R^5$, $R^6$ and m are the same as defined above); $R_g^1$ is a hydrogen atom, a hydroxyl group, a lower alkoxy group, a lower alkenyloxy group, a lower alkynyloxy group, a 2-tetrahydropyranyloxy group or a group of the formula,

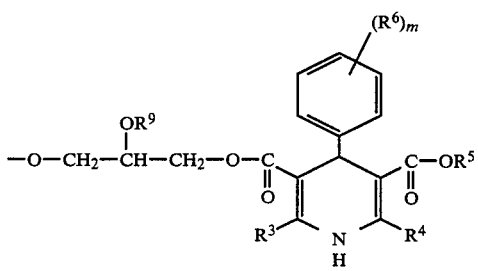

(wherein $R^3$, $R^4$, $R^5$, $R^6$ and m are the same as defined above; and $R^9$ is a lower alkanoyl group); $R_h^1$ is a hydrogen atom, a hydroxyl group, a lower alkoxy group, a lower alkenyloxy group, a lower alkynyloxy group, a 2-tetrahydrophranyloxy group or a group of the formula,

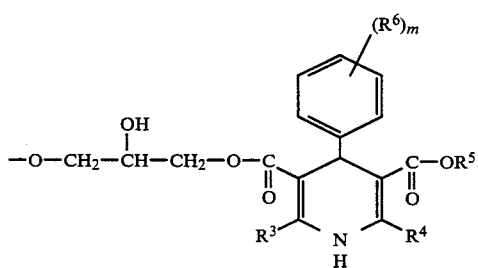

(wherein $R^3$, $R^4$, $R^5$, $R^6$ and m are the same as defined above); $R_g^2$ is a hydrogen atom, a lower alkyl group or a group of the formula,

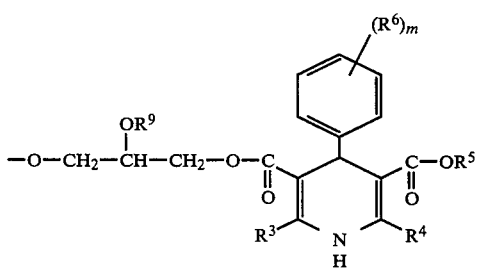

(wherein $R^3$, $R^4$, $R^5$, $R^6$, $R^9$ and m are defined above); $R_h^2$ is a hydrogen atom, a lower alkyl group or a group of the formula, (wherein $R^3$, $R^4$, $R^5$, $R^6$, $R^9$ and m are defined above); provided that, among $R_g$, $R_g^1$, and $R_g^2$, only one of them should be a group of the formula,

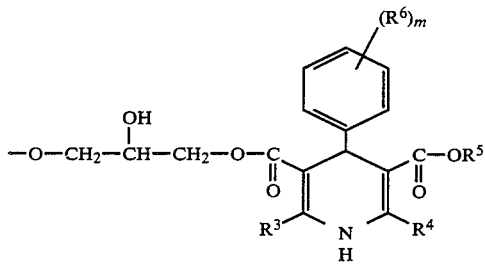

(wherein $R^3$, $R^4$, $R^5$, $R^6$ and m are the same as defined above); further, among $R_h{}^1$ and $R_h{}^2$, only one of them should be a group of the formula,

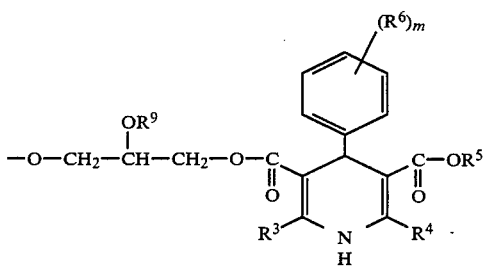

(wherein $R^3$, $R^4$, $R^5$, $R^6$, $R^9$ and m are the same as defined above)].

The reaction of a compound (6) with an epihalogenohydrin (15) can be carried out in the absence or presence of a suitable solvent, and in the presence of a basic compound.

As to the basic compound used in this reaction, inorganic basic compounds such as potassium hydroxide, sodium hydroxide, potassium carbonate, sodium carbonate, sodium methylate, sodium ethylate, sodium hydride, sodium metal, potassium metal and sodium amide; and organic basic compounds such as piperidine, pyridine and triethylamine can be examplified.

As to the solvent used in this reaction, lower alcohols such as methanol, ethanol and isopropanol; ketones such as acetone and methyl ethyl ketone; ethers such as diethyl ether, dioxane, diethylene glycol dimethyl ether; aromatic hydrocarbons such as benzene, toluene and xylene; water, dimethylformamide, dimethyl sulfoxide and hexamethylphosphoryl triamide; and mixed solvents thereof can be exemplified.

The ratio of the amount of the compound (15) to the amount of the compound (6), in this reaction, is usually an equimolar quantity to a large excess amount, preferably 5 to 10 times the molar quantities of the former to the latter.

The reaction is generally carried out at a temperature ranging from 0° C. to 150° C., preferably at room temperature to 100° C., and is completed in 10 minutes to 30 hours.

The reaction of the compound (16) with the compound (2) can be carried out in the absence or presence of an inert solvent at room temperature to 200° C., preferably at 60° C. to 120° C., and is completed in a several hours to 24 hours.

As to the solvent used in the reaction, any solvent which does not give any adverse effect to the reaction can be used, for example esters, aromatic hydrocarbons, lower alcohols, and aprotic polar solvents such as dimethylformamide, dimethyl sulfoxide and hexamethylphosphoryl triamide used in the reaction of the compound (6) with the compound (11) can also be used.

As to the basic compound used in this reaction, the examples include inorganic compounds such as potassium carbonate, sodium carbonate, sodium hydroxide, sodium hydrogencarbonate, sodium amide, and sodium hydride; and organic basic compounds such as triethylamine, tripropylamine, pyridine and quinoline.

The ratio of the amount of the compound (2) to the amount of the compound (16) is generally an equimolar quantity to a large excess quantity, preferably an equimolar quantity to 5 times the molar quantity and, the most preferably, an equimolar quantity to 1.2 times the molar quantity of the former to the latter.

The acylation reaction of the compound (13) can be carried out in the presence of an acylating agent such as a lower alkonoic acid, for example acetic acid or propionic acid; a lower alkanoic acid anhydride, for example acetic anhydride, or a lower alkanoic acid halide, for example acetyl chloride or propionyl bromide. In case of using an acid anhydride or an acid halide as the acylating agent, the acylating reaction is carried out in the presence of a basic compound. As to the basic compound used in this acylating reaction, the examples include alkali metals such as sodium metal and potassium metal; hydroxides, carbonates and hydrogencarbonates of these alkali metals; and aromatic amine compounds such as pyridine and piperidine. The acylation reaction can either proceed in the absence or presence of a solvent, and generally the reaction is carried out in the presence of a suitable solvent. As to the solvent, a ketone such as acetone or methyl ethyl ketone; an ether such as dioxane; an aromatic hydrocarbon such as benzene, toluene or xylene; water or pyridine can be exemplified.

The acylating agent is used in at least an equimolar quantity to the starting material, and generally an equimolar quantity to a large excess quantity of the acylating agent is used relative to the starting material. The reaction proceeds at 0° to 150° C., and generally may be carried out at 0° to 80° C. The reaction is completed in about 0.5 to 20 hours.

In case of using a lower alkanoic acid as the acylating agent, the acylating reaction can advantageously proceed by adding a mineral acid such as sulfuric acid or hydrohyloric acid; or a sulfonic acid such as p-toluenesulfonic acid, benzenesulfonic acid or ethanesulfonic acid as the dehydrating agent in the reaction system, and by keeping the reaction temperature preferably at 50° to 120° C.

The following is a description of Reaction scheme

Reaction scheme - 7

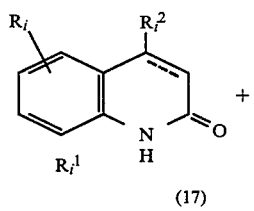

(17)

-continued
Reaction scheme - 7

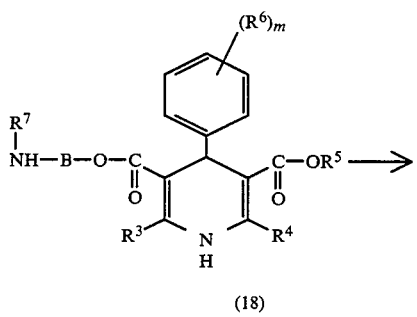

(18)

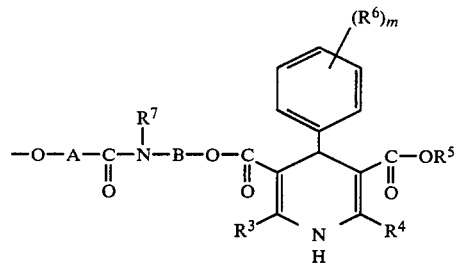

(wherein $R^3$, $R^4$, $R^5$, $R^6$, $R^7$, A, B and m are the same as defined above); $R_j^2$ is a hydrogen atom, a lower alkyl group or a group of the formula,

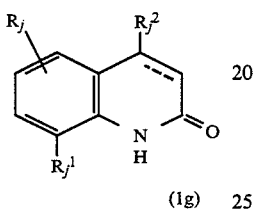

(Ig)

[wherein $R^3$, $R^4$, $R^5$, $R^6$, $R^7$, B, m and the carbon-carbon bond between 3- and 4-positions in the carbostyril skeleton are the same as defined above; $R_i$ is a hydrogen atom or a group of the formula,

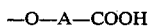
—O—A—COOH (wherein A is the same as defined above); $R_i^1$ is a hydrogen atom, a hydroxyl group, a lower alkoxy group, a lower alkenyloxy group, a lower alkynyloxy group, a 2-tetrahydropyranyloxy group or a group of the formula,

—O—A—COOH (wherein A is the same as defined above); $R_i^2$ is a hydrogen atom, a lower alkyl group or a group of the formula, —O—A—COOH (wherein A is the same as defined above); $R_j$ is a hydrogen atom or a group of the formula,

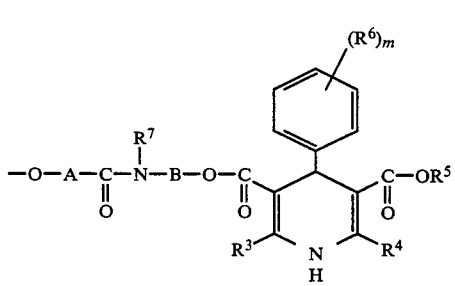

(wherein $R^3$, $R^4$, $R^5$, $R^6$, $R^7$, A, B and m are the same as defined above); $R_j^1$ is a hydrogen atom, a hydroxyl group, a lower alkoxy group, a lower alkenyloxy group, a lower alkynyloxy group, a 2-tetrahydropyranyloxy group or a group of the formula,

—O—A—COOH (wherein $R^3$, $R^4$, $R^5$, $R^6$, $R^7$, A, B and m are the same as defined above); provided that, among $R_i$, $R_i^1$ and $R_i^2$, only one of them should be a group of the formula,

—O—A—COOH (wherein A is the same as defined above); further, among $R_j$, $R_j^1$ and $R_j^2$, only one of them should be a group of the formula,

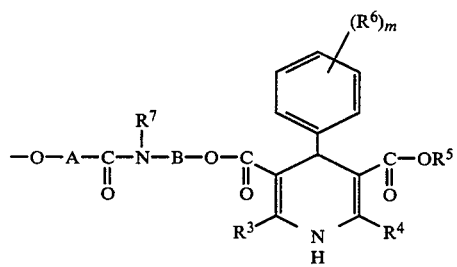

(wherein $R^3$, $R^4$, $R^5$, $R^6$, $R^7$, A, B and m are the same as defined above)].

The reaction as shown in the above-mentioned Reaction scheme—7 is a process for reacting a carboxyalkoxycarbostyril derivative (17) with an amine (18) by a conventional amide-bond formation reaction. In the present invention, any carboxyalkoxycarbostyril compound in which the carboxy group is activated may be used in place of a compound represented by the general formula (17).

In carrying out the amide-bond formation reaction, conventional amide-bond formation reaction conditions can easily be applied. Examples include (a) a mixed acid anhydride method: in which a carboxylic acid (17) is reacted with an alkylhalocarboxylic acid to prepare the corresponding mixed acid anhydride, then an amine (18) is reacted therewith; (b) activated ester method: in which a carboxylic acid (17) is converted into the corresponding activated ester, for example p-nitrophenyl ester, N-hydroxysuccimide ester or 1-hydroxybenzotriazole ester, then an amine (18) is reacted therewith; (c) dehydrocondensation method: in which a carboxylic acid (17) is reacted with an amine (18) in the presence of a dehydrating agent by a method of dehydrocondensation; and (d) other methods: for example, a method in which a carboxylic acid (17) is treated with a dehydrating agent such as acetic anhydride to obtain a carboxylic acid anhydride, then an amine (18) is reacted with said carboxylic acid anhydride; a method in which an ester prepared by reacting a carboxylic acid (17) with a lower alcohol is reacted with an amine (18) at a high temperature under a high pressure; and a method in which a carboxylic acid halide, i.e., an acid halogenide of a carboxylic acid (17) is reacted with an amine (18). Among these methods, (a) a mixed acid anhydride method and (c) dehycro-condensation method are preferable.

As to the alkylhalocarboxylic acid used in the mixed acid anhydride method, methyl chloroformate, methyl bromoformate, ethyl chloroformate, ethyl bromoformate or isobutyl chloroformate can be exemplified. The mixed acid anhydride can generally be prepared by a Schotten-Baumann reaction, and the mixed acid anhydride is reacted with an amine (18) without separated from the reaction system to prepare the compound of the present invention. The Schotten-Baumann reaction is carried out in the presence of a basic compound. As to the basic compound used in this reaction, any compound used customarily in a Schotten-Baumann reaction may be used, for example, an organic basic compound such as triethylamine, trimethylamine, pyridine, dimethylaniline, N-methylmorpholine, 1,5-diazabycyclo[4,3,0]nonene-5 (DBN), 1,5-diazabicyclo[5,4,0]undecene-5 DBU) or 1,4-diazabicyclo[2,2,2]octane (DABCO); or an inorganic basic compound such as potassium carbonate, sodium carbonate, potassium hydrogencarbonate or sodium hydrogencarbonate can be exemplified.

This reaction is carried out at −20° to 100° C., preferably at 0° to 50° C., and the reaction time is 5 minutes to 10 hours, preferably 5 minutes to 2 hours. Next, the reaction of the mixed acid anhydride thus obtained with an amine (18) is carried out at −20° to 150° C., preferably at 10° to 50° C., and the reaction time is 5 minutes to 10 hours, preferably 5 minutes to 5 hours.

The mixed acid anhydride method is generally carried out in a suitable solvent. As to the solvent used in this reaction, any solvent customarily used in a mixed acid anhydride method can also be used, for example, a halogenated hydrocarbon such methylene chloride, chloroform or dichloroethane; an aromatic hydrocarbon such as benzene, toluene or xylene; an ether such as diethyl ether, tetrahydrofuran or dimethoxyethane; an ester such as methyl acetate or ethyl acetate; or an aprotic polar solvent such as N,N-dimethylformamide, dimethyl sulfoxide or hexamethylphosphoryl triamide can be exemplified.

The ratio of the amounts of a carboxylic acid (17), an alkylhalocarboxylic acid and an amine (18) is generally at least an equimolar quantity each of an alkylhalocarboxylic acid and an amine (18) to the amount of a carboxylic acid (17); preferably 1 to 1.5 times the molar quantities each of an alkylhalocarboxylic acid and an amine (18) are used relative to the amount of a carboxylic acid (17).

As to the dehydrating agent used in the dehydrocondensation method, there is not any specific restriction thereto and any dehydrating agent can be used; specifically, N,N-dicyclohexylcarbodiimide (DCC), DCC-N-hydroxy succinimide (HOSU), DCC-N-hydroxybenzotriazole (HOBT), DCC-N-hydroxy-5-norbornene-2,3-dicarboxyimide (HONB), diphenylphosphoryl amide (DPPA) or diethylphosphoryl cyanidate (DEPC) can be exemplified.

Similar to the reaction of the mixed acid anhydride with an amine (18), this reaction can also be carried out in a solvent in the presence of the above-mentioned dehydrating agent at −20° to 200° C., preferably at 0° to 150° C., for about generally 5 minutes to 20 hours. The ratio of the amount of carboxylic acid (17) to the amount of an amine (18) is generally at least an equimolar quantity; preferably 1 to 1.5 times the molar quantity of the amine (18) is used relative to the amount of the carboxylic acid (17). The ratio of the amount of the dehydrating agent is not specifically restricted, and generally, at least an equimolar quantity, preferably an equimolar quantity to 1.5 times the molar quantity of the dehydrating agent may be used relative to the amount of the carboxylic acid.

Amines (18) used as the starting materials in the above-mentioned Reaction scheme—7 contain novel compounds which can be prepared by a method as shown in the following Reaction scheme—8.

Reaction scheme - 8

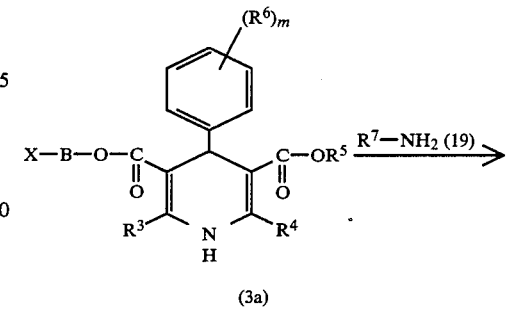

(3a)

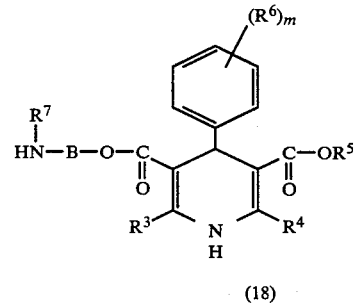

(18)

(wherein $R^3$, $R^4$, $R^5$, $R^6$, $R^7$, B, X and m are the same as defined above).

The reaction of a compound (3a) with a compound (19) can be carried out under conditions similar to those employed in the reaction of a compound (2) with a compound (3) in the above-mentioned Reaction scheme—1.

In the above-mentioned Reaction scheme—1, compound (3) as used for the starting material, wherein n=1 can be prepared by a method as shown in the following Reaction scheme—9.

Reaction scheme - 9

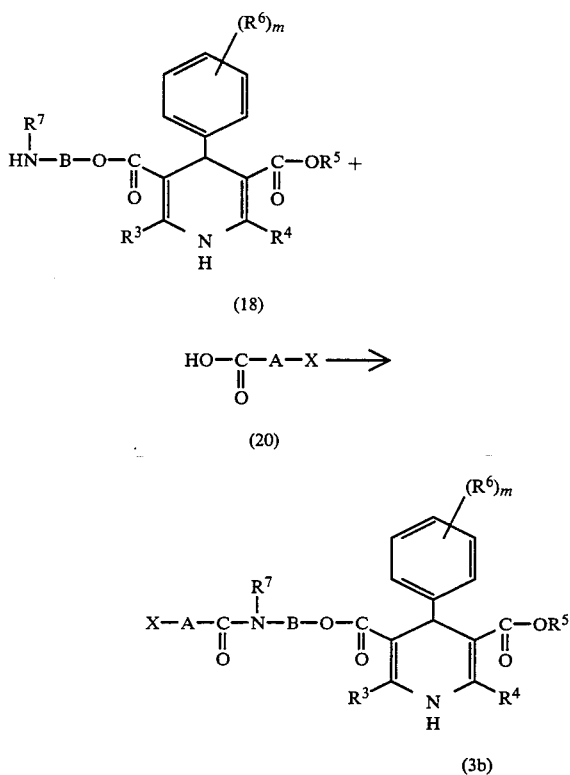

(wherein $R^3$, $R^4$, $R^5$, $R^6$, $R^7$, X, A, B and m are the same as defined above).

The reaction of a compound (18) with a compound (20) can be carried out under conditions similar to those employed in the amide bond formation reaction in the Reaction scheme—7.

Among carbostyril derivatives represented by the general formula (1), the compounds having a lower alkylene group A; which may have a lower alkanoyloxy group can be prepared by acylating a carbostyril derivative represented by the general formula (1) wherein A is a lower alkylene group which has a hydroxyl group as the substituent. This acylating reaction can be carried out under conditions employed in the acylating reaction of a compound (1f) in the Reaction scheme—6.

The compounds represented by the general formula (1) having the basic group can easily be converted into the corresponding salts by being treated with pharmaceutically acceptable acids. Examples of such acids include inorganic acids such as sulfuric acid, nitric acid, hydrochloric acid and hydrobromic acid.

Compounds of the present invention thus prepared can easily be isolated and purified by conventional methods of separation such as precipitation, extraction, recrystallization, column chromatography and preparative thin-layer chromatography.

Compounds of the present invention represented by the general formula also include their optical isomers.

Compounds of the present invention represented by the general formula can be administered, either singly or together with conventional pharmaceutically acceptable carriers, to animals as well as to humans. No particular restriction is made on the administration unit forms; thus a compound of the present invention represented by the general formula (1) can be used in any desired administration unit form. Suitable administration unit forms include oral administration forms such as tablets, granules and solutions; and parenteral administration unit forms such as injections.

The dosage of compounds represented by the general formula (1) as the active ingredient to be administered is not subjected to any particular restriction and can be selected from a wide range. For the purpose of attaining the desired pharmacological effects, it is recommended to select the dosage from the range of 0.06 to 10 mg per kg of body weight per day. It is also suggested to provide 1 to 500 mg of the compound of the present invention as the active ingredient in each of the desired administration unit form.

Compounds of the present invention can be shaped into the desired peroral preparation from such as tablets, capsules and solutions by use of conventional methods. For the purpose of shaping the composition into the form of tablets, the compound of the present invention is mixed with a pharmaceutically acceptable excipient such as gelatin, starch, lactose, magnesium stearate, talcum powder or gum arabic. Capsules can be prepared by mixing a compound of the present invention with inert pharmaceutically acceptable fillers or diluents and filling the mixture obtained into rigid gelatin capsules or soft capsules. Syrups or elixiers may be prepared by mixing a compound of the present invention with a sweetening agent such as sucrose; antisceptics such as methyl- or propyl-parabens; colorants, seasoning agents and/or other suitable additives. Parenteral preparations can also be prepared by conventional methods; thus a compound of the present invention is dissolved in a sterilized liquid vehicle. As to preferable vehicles, water or saline water can be used. Liquid preparations having desired transparency, stability and parenteral use adaptability can be prepared by dissolving approximately 1 to 500 mg of the active ingredient in a solution of polyethylene glycol having a molecular weight of 200 to 5,000, which is soluble in both water and organic solvents. Desirably, such liquid preparations may contain a lubricant such as sodium carboxymethyl cellulose, methyl cellulose, polyvinyl pyrrolidone or polyvinyl alcohol. Said liquid preparations may also contain a bactericide and fungicide such as benzyl alcohol, phenol or thimerosal, and if necessary, an isotonic agent such as sucrose or sodium chloride, a local anesthetic stabilizer and buffer solutions. For further additional ensurance of stability, the parenteral compositions may be frozen after filling and dehydrating by known lyophilization techniques. The lyophilized powder of the parenteral composition can be reconstituted into a normal use form just before the use.

Preparation of tablets-1

1,000 Tablets for peroral use, each containing 5 mg of 5-{2-[2,6-dimethyl-5-methoxycarbonyl-4-(3-nitrophenyl)-1,4-dihydropyridin-3-carboxy]ethoxy}carbostyril, are prepared from the following ingredients.

| Ingredient | Amount (g) |
| --- | --- |
| 5-{2-[2,6-Dimethyl-5-methoxy-carbonyl-4-(3-nitrophenyl)-1,4-dihydropyridin-3-carboxy]ethoxy}-carbostyril | 5 |
| Lactose (Japanese Pharmacopoeia) | 50 |
| Corn starch (Japanese Pharmacopoeia) | 25 |

| Ingredient | Amount (g) |
| --- | --- |
| Crystalline cellulose (Japanese Pharmocopoeia) | 25 |
| Methylcellulose (Japanese Pharmocopoeia) | 1.5 |
| Magnesium stearate (Japanese Pharmocopoeia) | 1 |

The 5-{2-[2,6-dimethyl-5-methoxycarbonyl-4-(3-nitrophenyl-1,4-dihydropyridin-3-carboxy]ethoxy}carbostyril, lactose, corn starch and crystalline cellulose are mixed well, and the mixture is added to a 5%-aqueous solution of methyl cellulose and then granulated. The granules obtained are passed through a 200 mesh sieve and then dried carefully. The dried granules are mixed with magnesium stearate through a 200 mesh sieve then pressed into the form of tablets.

Preparation of tablets-2

1,000 Tablets for peroral use, each containing 5 mg of 6-{3-[2,6-dimethyl-5-methoxycarbonyl-4-(3-nitrophenyl)-1,4-dihydropyridin-3-carboxy]-2-hydroxypropoxy}-3,4-dihydrocarbostyril are prepared from the following ingredients, by a method similar to that described in the above-mentioned Preparation of tablets-1.

| Ingredient | Amount (g) |
| --- | --- |
| 6-{3-[2,6-Dimethyl-5-methoxycarbonyl-4-(3-nitrophenyl)-1,4-dihydropyridin-3-carboxy]-2-hydroxypropoxy}-3,4-dihydrocarbostyril | 5 |
| Lactose (Japanese Pharmacopoeia) | 50 |
| Corn starch (Japanese Pharmacopoeia) | 25 |
| Crystalline cellulose (Japanese Pharmacopoeia) | 25 |
| Methylcellulose (Japanese Pharmocopoeia) | 1.5 |
| Magnesium stearate (Japanese Pharmacopoeia) | 1 |

Preparation of tablets-3

1,000 Tablets for peroral use, each containing 5 mg of N-{2-[1,4-dihydro-2,6-dimethyl-5-methoxycarbonyl-4-(3-nitrophenyl)pyridin-3-carboxy]ethyl}-N-cyclohexyl-4-(6-carbostyriloxy)butyramide are prepared from the following ingredients, by a method similar to that described in the above-mentioned Preparation of tablets-1.

| Ingredient | Amount (g) |
| --- | --- |
| N—{2-[1,4-Dihydro-2,6-dimethyl-5-methoxycarbonyl-4-(3-nitrophenyl)-pyridin-3-carboxy]ethyl}-N—cyclohexyl-4-(6-carbostyriloxy)butyramide | 5 |
| Lactose (Japanese Pharmacopoeia) | 50 |
| Corn starch (Japanese Pharmacopoeia) | 25 |
| Crystalline cellulose (Japanese Pharmacopoeia) | 25 |
| Methyl cellulose (Japanese Pharmacopoeia) | 1.5 |
| Magnesium stearate (Japanese Pharmacopoeia) | 1 |

Preparation of capsules-1

1,000 Capsules of two-piece rigid gelatin capsules for peroral use, each containing 10 mg of 6-{2-[2,6-dimethyl-5-methoxycarbonyl-4-(3-nitrophenyl)-1,4-dihydropyridin-3-carboxy]ethoxy}carbostyril, are filled using the following ingredients.

| Ingredient | Amount (g) |
| --- | --- |
| 6-{2-[2,6-Dimethyl-5-methoxycarbonyl-4-(3-nitrophenyl)-1,4-dihydropyridin-3-carboxy]ethoxy}carbostyril | 10 |
| Lactose (Japanese Pharmocopoeia) | 80 |
| Starch (Japanese Pharmacopoeia) | 30 |
| Talcum powder (Japanese Pharmacopoeia) | 5 |
| Magnesium stearate (Japanese Pharmacopoeia) | 1 |

The above components are finely ground, then stirred and mixed sufficiently to a uniform mixture and then filled into gelatin capsules of a size convenient for peroral administration.

Preparation of capsules-2

1,000 Capsules of two-piece rigid geleatin capsules for peroral use, each containing 10 mg of 5-{3-[2,6-dimethyl-5-methoxycarbonyl-4-(3-nitrophenyl)-1,4-dihydropyridin-3-carboxy]propoxy}-8-propoxy-3,4-dihydrocarbostyril, are filled using the following ingredients.

| Ingredient | Amount (g) |
| --- | --- |
| 5-{3-[2,6-Dimethyl-5-methoxycarbonyl-4-(3-nitrophenyl)-1,4-dihydropyridin-3-carboxy]propoxy}-8-propoxy-3,4-dihydrocarbostyril | 10 |
| Lactose (Japanese Pharmacopoeia) | 80 |
| Starch (Japanese Pharmacopoeia) | 30 |
| Talcum powder (Japanese Pharmacopoeia) | 5 |
| Magnesium stearate (Japanese Pharmacopoeia) | 1 |

The above components are finely ground, then stirred and mixed sufficiently to a uniform mixture and then filled into gelatin capsules of a size convenient for peroral administration.

Preparation of capsules-3

1,000 Capsules of two-piece rigid gelatin capsules for peroral use, each containing 10 mg of 6-{3-[2,6-dimethyl-5-methoxycarbonyl-4-(3-nitrophenyl)-1,4-dihydropyridin-3-carboxy]2-acetoxypropoxy}-3,4-dihydrocarbostyril, are filled using the following ingredients, by a method similar to that described in Preparation of capsules-1.

| Ingredient | Amount (g) |
| --- | --- |
| 6-{3-[2,6-Dimethyl-5-methoxycarbonyl-4-(3-nitrophenyl)-1,4-dihydropyridin-3-carboxy]-2-acetoxypropoxy}-3,4-dihydrocarbostyril | 10 |
| Lactose (Japanese Pharmacopoeia) | 80 |
| Starch (Japanese Pharmacopoeia) | 30 |
| Talcum powder (Japanese Pharmacopoeia) | 5 |
| Magnesium stearate (Japanese Pharmacopoeia) | 1 |

Preparation of capsules-4

1,000 Capsules of two-piece rigid gelatin capsules for peroral use, each containing 10 mg of 6-{4-[2,6-dimethyl-5-methoxycarbonyl-4-(2-methylthiophenyl)-1,4-dihydropyridin-3-carboxy]butoxy}-3,4-dihydrocarbostyril, are filled using the following ingredients, by a method similar to that described in Preparation of capsules-1.

| Ingredient | Amount (g) |
| --- | --- |
| 6-{4-[2,6-Dimethyl-5-methoxycarbonyl-4-(2-methylthiophenyl)-1,4-dihydro-pyridin-3-carboxy]butoxy}-3,4-dihydrocarbostyril | 10 |
| Lactose (Japanese Pharmacopoeia) | 80 |
| Starch (Japanese Pharmacopoeia) | 30 |
| Talcum powder (Japanese Pharmacopoeia) | 5 |
| Magnesium stearate (Japanese Pharmacopoeia) | 1 |

Preparation of capsules-5

1,000 Capsules of two-piece rigid geletin capsules for peroral use, each containing 10 mg of N-{2-[2,6-dimethyl-5-methoxycarbonyl-4-(2-nitrophenyl)-1,4-dihydropyridin-3-carboxy]ethyl}-N-cyclohexyl-4-(6-carbostyriloxy)butyramide, are filled using the following ingredients, by a method similar to that described in Preparation of capsules-1.

|  | Amount (g) |
| --- | --- |
| N—{2-[1,4-Dihydro-2,6-dimethyl-5-methoxycarbonyl-4-(2-nitrophenyl)-pyridin-3-carboxy]ethyl}-N—cyclohexyl-4-(6-carbostyriloxy)-butyramide | 10 |
| Lactose (Japanese Pharmacopoeia) | 80 |
| Starch (Japanese Pharmacopoeia) | 30 |
| Talcum powder (Japanese Pharmacopoeia) | 5 |
| Magnesium stearate (Japanese Pharmacopoeia) | 1 |

Preparation of capsules-6

1,000 Capsules of two-piece rigid gelatin capsules for peroral use, each containing 10 mg of N-[2-(1,4-dihydro-2,6-dimethyl-5-methoxycarbonyl-4-phenylpyridin-3-carboxy)ethyl]-N-cyclohexyl-1-4-(6-carbostyriloxy)-butyramide, are filled using the following ingredients, by a method similar to that described in Preparation of capsules-1.

| Ingredient | Amount (g) |
| --- | --- |
| N—[2-(1,4-Dihydro-2,6-dimethyl-5-methoxycarbonyl-4-phenylpyridin-3-carboxy)ethyl]-N—cyclohexyl-4-(6-carbostyriloxy)butyramide | 10 |
| Lactose (Japanese Pharmacopoeia) | 80 |
| Starch (Japanese Pharmacopoeia) | 30 |
| Talcum powder (Japanese Pharmacopoeia) | 5 |
| Magnesium stearate (Japanese Pharmacopoeia) | 1 |

Preparation of injections-1

A sterile aqueous solution suited for parenteral use is prepared from the following ingredients.

| Ingredient | Amount (g) |
| --- | --- |
| 5-{3-[2,6-Dimethyl-5-methoxycarbonyl-4-(3-nitrophenyl)-1,4-dihydropyridin-3-carboxy]propoxy}-8-hydroxy-3,4-dihydrocarbostyril | 1 |
| Polyethylene glycol (Molecular weight: 4,000) (Japanese Pharmacopoeia) | 0.9 |
| Sodium chloride (Japanese Pharmacopoeia) | 0.9 |
| Polyoxyethylene sorbitan monooleate (Japanese Pharmacopoeia) | 0.4 |
| Sodium metabisulfite | 0.1 |
| Methyl p-hydroxybenzoate (Japanese Pharmacopoeia) | 0.18 |
| Propyl p-hydroxybenzoate (Japanese Pharmacopoeia) | 0.02 |
| Distilled water for injection | 100 (ml) |

A mixture of methyl p-hydroxybenzoate, propyl p-hydroxybenzoate, sodium metabisulfite and sodium chloride is dissolved with stirring in about half the quantity of distilled water at 80° C. The solution obtained is cooled to 40° C., and then the 5-{3-[2,6-dimethyl-5-methoxycarbonyl-4-(3-nitrophenyl)-1,4-dihydroxypyridin-3-carboxy]propoxy}-8-hydroxy-3,4-dihydrocarbostyril, polyethylene glycol and polyoxyethylene sorbitan monooleate are dissolved in that order in the solution. This solution is further mixed with water to the final regulated volume for injection and then sterilized by sterile filtration with suitable filter paper.

Preparation of injections-2

A sterile aqueous solution suited for parenteral use is prepared from the following ingredients.

| Ingredient | Amount (g) |
| --- | --- |
| 6-{4-[2,6-Dimethyl-5-methoxycarbonyl-4-(2-trifluoromethylphenyl)-1,4-dihydropyridin-3-carboxy]butoxy}-carbostyril | 1 |
| Polyethylene glycol (Molecular weight: 4,000) (Japanese Pharmacopoeia) | 0.9 |
| Sodium chloride (Japanese Pharmacopoeia) | 0.9 |
| Polyoxyethylene sorbitan monooleate (Japanese Pharmacopoeia) | 0.4 |
| Sodium metabisulfite | 0.1 |
| Methyl p-hydroxybenzoate | 0.18 |
| (Japanese Pharmacopoeia) | 0.18 |
| Propyl p-hydroxybenzoate (Japanese Pharmacopoeia) | 0.02 |
| Distilled water for injection | 100 (ml) |

The injection preparations were prepared by a method similar to that described in Preparation of injections-1.

Preparation of injections-3

A sterile aqueous solution suited for parenteral use is prepared from the following ingredients, by a method similar to that described in Preparation of injections-1.

| Ingredient | Amount (g) |
| --- | --- |
| N—{2-[1,4-Dihydro-2,6-dimethyl-5-methoxycarbonyl-4-(3-nitrophenyl)-pyridin-3-carboxy]ethyl}-N—cyclohexyl-4-(3,4-dihydrocarbostyril- | 1 |

| Ingredient | Amount (g) |
| --- | --- |
| 6-yl)oxybutyramide | |
| Polyethylene glycol | 0.3 |
| (Molecular weight: 4,000) | |
| (Japanese Pharmacopoeia) | |
| Sodium chloride | 0.9 |
| (Japanese Pharmacopoeia) | |
| Polyoxyethylene sorbitan monooleate | 0.4 |
| (Japanese Pharmacopoeia) | |
| Sodium metabisulfite | 0.1 |
| Methyl p-hydroxybenzoate | 0.18 |
| (Japanese Pharmacopoeia) | |
| Propyl p-hydroxybenzoate | 0.02 |
| (Japanese Pharmacopoeia) | |
| Distilled water for injection | 100 (ml) |

Pharmacological tests

The results of the pharmacological tests on compounds of the present invention are shown below.

Tested compounds used in the pharmacological tests are as follows:

| Tested Compound No. | |
| --- | --- |
| 1. | 5-{3-[2,6-Dimethyl-5-methoxycarbonyl-4-(3-nitrophenyl)-1,4-dihydropyridin-3-carboxy]-propoxy}-8-propenyloxy-3,4-dihydrocarbostyril |
| 2. | 5-{2-[2,6-Dimethyl-5-methoxycarbonyl-4-(3-nitrophenyl)-1,4-dihydropyridin-3-carboxy]-ethoxy}-3,4-dihydrocarbostyril |
| 3. | 6-{2-[2,6-Dimethyl-5-methoxycarbonyl-4-(3-nitrophenyl)-1,4-dihydropyridin-3-carboxy]-ethoxy}-3,4-dihydrocarbostyril |
| 4. | 5-{3-[2,6-Dimethyl-5-methoxycarbonyl-4-(3-nitrophenyl)-1,4-dihydropyridin-3-carboxy]-propoxy}-3,4-dihydrocarbostyril |
| 5. | 6-{3-[2,6-Dimethyl-5-methoxycarbonyl-4-(3-nitrophenyl)-1,4-dihydropyridin-3-carboxy]-propoxy}-3,4-dihydrocarbostyril |
| 6. | 7-{3-[2,6-Dimethyl-5-methoxycarbonyl-4-(3-nitrophenyl)-1,4-dihydropyridin-3-carboxy]-propoxy}-3,4-dihydrocarbostyril |
| 7. | 5-{3-[2,6-Dimethyl-5-methoxycarbonyl-4-(3-nitrophenyl)-1,4-dihydropyridin-3-carboxy]-propoxy}-8-hydroxy-3,4-dihydrocarbostyril |
| 8. | 6-{3-[2,6-Dimethyl-5-methoxycarbonyl-4-(3-nitrophenyl)-1,4-dihydropyridin-3-carboxy]-propoxy}carbostyril |
| 9. | 8-{3-[2,6-Dimethyl-5-methoxycarbonyl-4-(3-nitrophenyl)-1,4-dihydropyridin-3-carboxy]-propoxy}-3,4-dihydrocarbostyril |
| 10. | 6-{2-[2,6-Dimethyl-5-methoxycarbonyl-4-(3-nitrophenyl)-1,4-dihydropyridin-3-carboxy]-ethoxy}carbostyril |
| 11. | 5-{3-[2,6-Dimethyl-5-methoxycarbonyl-4-(3-nitrophenyl)-1,4-dihydropyridin-3-carboxy]-propoxy}-8-propoxy-3,4-dihydrocarbostyril |
| 12. | 5-{3-[2,6-Dimethyl-5-methoxycarbonyl-4-(3-nitrophenyl)-1,4-dihydropyridin-3-carboxy]-propoxy}-8-(2-propynyloxy)-3,4-dihydrocarbostyril |
| 13. | 8-{2-[2,6-Dimethyl-5-methoxycarbonyl-4-(3-nitrophenyl)-1,4-dihydropyridin-3-carboxy]-ethoxy}-3,4-dihydrocarbostyril |
| 14. | 7-{2-[2,6-Dimethyl-5-methoxycarbonyl-4-(3-nitrophenyl)-1,4,-dihydropyridin-3-carboxy]-ethoxy}-3,4-dihydrocarbostyril |
| 15. | 6-{4-[2,6-Dimethyl-5-methoxycarbonyl-4-(3-nitrophenyl)-1,4-dihydropyridin-3-carboxy]-butoxy}carbostyril |
| 16. | 6-{4-[2,6-Dimethyl-5-methoxycarbonyl-4-(3-nitrophenyl)-1,4-dihydropyridin-3-carboxy]-butoxy}-3,4-dihydrocarbostyril |
| 17. | 5-{4-[2,6-Dimethyl-5-methoxycarbonyl-4-(3-nitrophenyl)-1,4-dihydropyridin-3-carboxy]-butoxy}-3,4-dihydrocarbostyril |
| 18. | 5-{4-[2,6-Dimethyl-5-methoxycarbonyl-4-(3-nitrophenyl)-1,4-dihydropyridin-3-carboxy]-butoxy}carbostyril |
| 19. | 5-{4-[2,6-Dimethyl-5-methoxycarbonyl-4-(3-nitrophenyl)-1,4-dihydropyridin-3-carboxy]-butoxy}-8-alloyloxy-3,4-dihydrocarbostyril |
| 20. | 6-{2-[2,6-Dimethyl-5-methoxycarbonyl-4-(2-nitrophenyl)-1,4-dihydropyridin-3-carboxy]-ethoxy}carbostyril |
| 21. | 6-{2-[2,6-Dimethyl-5-methoxycarbonyl-4-(2-nitrophenyl)-1,4-dihydropyridin-3-carboxy]-ethoxy}-3,4-dihydrocarbostyril |
| 22. | 5-{3-[2,6-Dimethyl-5-methoxycarbonyl-4-(3-nitrophenyl)-1,4-dihydropyridin-3-carboxy]-propoxy}carbostyril |
| 23. | 6-{3-[2,6-Dimethyl-5-methoxycarbonyl-4-(3-nitrophenyl)-1,4-dihydropyridin-3-carboxy]-2-acetoxypropoxy}-3,4-dihydrocarbostyril |
| 24. | 6-{4-[2,6-Dimethyl-5-methoxycarbonyl-4-(2-trifluoromethylphenyl)-1,4-dihydropyridin-3-carboxy]butoxy}carbostyril |
| 25. | 6-{4-[2,6-Dimethyl-5-methoxycarbonyl-4-(2-trifluoromethylphenyl)-1,4-dihydropyridin-3-carboxy]butoxy}-3,4-dihydrocarbostyril |
| 26. | 6-{4-[2,6-Dimethyl-5-methoxycarbonyl-4-(2-methylthiophenyl)-1,4-dihydropyridin-3-carboxy]butoxy}-3,4-dihydrocarbostyril |
| 27. | 6-{4-[2,6-Dimethyl-5-methoxycarbonyl-4-(2-chlorophenyl)-1,4-dihydropyridin-3-carboxy]-butoxy}-3,4-dihydrocarbostyril |
| 28. | 6-[4-(2,6-Dimethyl-5-methoxycarbonyl-4-phenyl-1,4-dihydropyridin-3-carboxy)butoxy] -3,4-dihydrocarbostyril |
| 29. | 6-{4-[2,6-Dimethyl-5-methoxycarbonyl-4-(2-methylphenyl-1,4-dihydropyridin-3-carboxy)]-butoxy}-3,4-dihydrocarbostyril |
| 30. | 6-{4-[2,6-Dimethyl-5-methoxycarbonyl-4-(2-methoxycarbonyl)-1,4-dihydropyridin-3-carboxy]butoxy}-3,4-dihydrocarbostyril |
| 31. | N—{2-[1,4-Dihydro-2,6-dimethyl-5-methoxycarbonyl-4-(3-nitrophenyl)pyridin-3-carboxy]ethyl}-N—cyclohexyl-4-(6-carbostyriloxy)butyramide |
| 32. | N—{2-[1,4-Dihydro-2,6-dimethyl-5-methoxycarbonyl-4-(2-nitrophenyl)pyridin-3-carboxy]ethyl}-N—cyclohexyl-4-(3,4-dihydro-6-carbostyriloxy)-butyramide |
| 33. | N—{2-[1,4-Dihydro-2,6-dimethyl-5-methoxycarbonyl-4-(3-nitrophenyl)pyridin-3-carboxy]ethyl}-N—cyclohexyl-4-(5-carbostyriloxy)butyramide |
| 34. | N—{2-[1,4-Dihydro-2,6-dimethyl-5-methoxycarbonyl-4-(2-nitrophenyl)pyridin-3-carboxy]ethyl}-N—cyclohexyl-4-(6-carbostyriloxy)butyramide |
| 35. | N—[2-(1,4-Dihydro-2,6-dimethyl-5-methoxycarbonyl-4-phenylpyridin-3-carboxy)ethyl]-N—cyclohexyl-4-(6-carbostyriloxy)butyramide |
| 36. | N—[2,(1,4-Dihydro-2,6-dimethyl-5-methoxycarbonyl-4-phenylpyridin-3-carboxy)ethyl]-N—ethyl-4-(6-carbostyriloxy)butyramide |
| 37. | 4-{3-[2,6-Dimethyl-5-methoxycarbonyl-4-(3-nitrophenyl)-1,4-dihydropyridin-3-carboxy]propoxy}carbostyril |
| 38. | 4-Methyl-6-{3-[2,6-dimethyl-5-methoxycarbonyl-4-(3-nitrophenyl)-1,4-dihydropyridin-3-carboxy]propoxy}carbostyril |
| 39. | 6-{3-[2,6-Dimethyl-5-methoxycarbonyl-4-(3-nitrophenyl)-1,4-dihydropyridin-3-carboxy]-2-hydroxypropoxy}-3,4-dihydrocarbostyril |
| 40. | 6-{4-[2,6-Dimethyl-5-methoxycarbonyl-4-(3,4-dimethoxyphenyl)-1,4-dihydropyridin-3-carboxy]butoxy}-3,4-dihydrocarbostyril |
| 41. | 6-{4-[2,6-Dimethyl-5-methoxycarbonyl-4-(3,4,5-trimethoxyphenyl)-1,4-dihydropyridin-3-carboxy] butoxy}-3,4-dihydrocarbostyril |
| 42. | 6-{4-[2,6-Dimethyl-5-methoxycarbonyl-4-(2,4-dichlorophenyl)-1,4-dihydropyridin-3-carboxy]butoxy}-3,4-dihydrocarbostyril |
| 43. | 6-{3-[2,6-Dimethyl-5-methoxycarbonyl-4-(3-nitrophenyl)-1,4-dihydropyridin-3- |

| Tested Compound No. | -continued |
| --- | --- |
| 44. | carboxy]-2-acetoxypropoxy}carbostyril<br>6-[3-(2,6-Dimethyl-5-methoxycarbonyl-4-phenyl-1,4-dihydropyridin-3-carboxy)propoxy]-carbostyril |

Pharmacological test-1

The platelet aggregation inhibitory effect was measured by using a Platelet Aggregation Tracer Model PAT-6M (manufactured by Nikoh Bio-Science Co., Ltd.) by a method according to Kimura, et al., [IGAKU-NO-AYUMI (Progress in Medicine), Vol. 114, No. 9, pp. 718–727, Aug. 30, 1980, and Nature, pp. 927–929, 1962].

The blood sample used for the test was a 1:9 (by volume) mixture of "3.8%-CITRATE" ® (a registered trademark for 3.8%-sodium citrate, manufactured by Green Cross Corp.) and whole blood collected from rabbits. Said sample was subjected to 10-minute centrifugal separation at 1,000 r.p.m. (200xG) to obtain a platelet rich plasma (PRP). The PRP thus obtained was separated, and the remaining blood sample was further subjected to 15-minute centrifugal separation at 3,000 r.p.m. (2,000xG) to obtain a platelet poor plasma (PPP).

The number of platelets in the PRP was counted by the Brecher-Clonkite Method, and the PRP was diluted with the PPP to prepare a PRP sample with a platelet concentration of 600,000/microliter to prepare for an adenosine diphosphate (ADP)-induced aggregation test, and a collagen-induced aggregation test. 0.2 Milliliter of the PRP sample was added to 2 microliters of a solution of a test compound of predetermined concentration and this mixture was placed in a 37° C. thermostat for one minute. Then 20 microliters of an ADP or collagen solution was added to the mixture. In this test, the ADP solution was prepared by adjustment to a concentration of $7.5 \times 10^{-5}$M by using Auren-Beronal buffer solution (pH 7.35). Further, the collagen solution was prepared by adjustment to a concentration of 200 micrograms/ml by using collagen reagent of "Holm" ® (manufactured by Hormon-Chemie Munchen, GmbH.) which was diluted wih a physiological saline solution.

The transmittance of the resultant test mixture was determined and the change of transmittance was recorded by using the aggregometer at a stirrer speed of 1,100 r.p.m.

The platelet aggregation inhibitory effect of the test compound was measured in terms of inhibition rate (%) with respect to the aggregation rate of the controls. The aggregation rate was calculated from the following formula.

Aggregation rate $= [(c-a)/(b-a)] \times 100$ wherein
 a: transmittance of PRP
 b: transmittance of PPP
 c: transmittance of PRP containing a test compound and aggregation inducer.

The percent inhibition is calculated from the following formula.

Inhibition rate (%) $= [(A-B)/A] \times 100$ wherein
A: aggregation rate of the control
B: aggregation rate of the test compound.

The inhibitory effect of the test compounds on collagen-induced aggregation in rabbit platelets is shown in Table 1, similarly such effect on ADP-induced aggregation in rabbit platelets is shown in Table 2.

TABLE 1

Inhibition rate (%) of collagen-induced aggregation

| Test Compound No. | Concentration of the test compound solution | |
| --- | --- | --- |
| | $10^{-4}$ mole | $10^{-5}$ mole |
| 1 | 51 | 15 |
| 2 | 79 | 17 |
| 3 | 100 | 97 |
| 4 | 23 | 11 |
| 5 | 38 | 12 |
| 6 | 19 | 3 |
| 7 | 15 | 3 |
| 8 | 99 | 27 |
| 9 | 16 | 2 |
| 10 | 100 | 50 |
| 11 | 10 | — |
| 12 | 10 | — |
| 15 | 100 | 26 |
| 18 | 100 | 3 |
| 19 | 17 | — |
| 20 | 100 | 100 |
| 21 | 100 | 99 |
| 22 | 100 | 21 |
| 23 | 100 | 29 |
| 24 | 100 | 30 |
| 26 | 100 | 19 |
| 27 | 61 | — |
| 28 | 63 | — |
| 29 | 69 | — |
| 30 | 100 | 3 |
| 31 | 100 | 100 |
| 32 | 100 | 34 |
| 33 | 100 | 34 |
| 34 | 100 | 100 |
| 35 | 100 | 100 |
| 36 | 100 | 100 |
| 37 | 15 | — |
| 38 | 45 | — |
| 39 | 100 | 19 |
| 40 | 15 | — |
| 41 | 35 | — |
| 42 | 39 | — |
| 43 | 100 | 100 |
| 44 | 100 | 25 |

TABLE 2

Inhibition rate (%) of ADP-induced aggregation

| Test Compound No. | Concentration of the test compound solution | |
| --- | --- | --- |
| | $10^{-4}$ mole | $10^{-5}$ mole |
| 1 | 19 | 1 |
| 2 | 28 | 1 |
| 3 | 100 | 27 |
| 4 | 16 | 4 |
| 5 | 20 | 4 |
| 6 | 15 | 6 |
| 7 | 14 | 3 |
| 8 | 76 | 10 |
| 9 | 12 | 7 |
| 10 | 100 | 27 |
| 11 | 11 | — |
| 12 | 14 | — |
| 15 | 100 | 20 |
| 18 | 48 | 15 |
| 19 | 17 | — |
| 20 | 100 | 65 |
| 21 | 58 | 27 |
| 22 | 62 | 13 |
| 23 | 79 | 29 |
| 24 | 100 | 62 |

TABLE 2-continued

Inhibition rate (%) of ADP-induced aggregation

| Test Compound No. | Concentration of the test compound solution | |
|---|---|---|
| | $10^{-4}$ mole | $10^{-5}$ mole |
| 26 | 87 | 22 |
| 27 | 42 | — |
| 28 | 52 | — |
| 29 | 59 | — |
| 30 | 89 | — |
| 31 | 100 | 84 |
| 32 | 98 | 25 |
| 33 | 98 | 25 |
| 34 | 94 | 98 |
| 35 | 100 | 89 |
| 36 | 98 | 55 |
| 37 | 17 | — |
| 38 | 31 | — |
| 39 | 76 | — |
| 40 | 14 | — |
| 41 | 30 | — |
| 42 | 26 | — |
| 43 | 100 | 100 |
| 44 | 100 | 20 |

Pharmacological test-2

The change of blood flow in coronary artery and the change of blood pressure were measured by a method according to Yakura et al., [Japan Journal of Pharmacology, Vol. 57, pages 380–391 (1961)] and according to Taira, et al. [Clin. Exp. Pharmacol. Physiol., Vol. 6, pages 301–316, (1976)].

An adult bastard dog of either sex weighing 8–13 kg was anesthetized with sodium pentobarbital at the rate of 30 mg/kg by intraveneous administration, then the dog was fixed in supination and was theracotomized under a condition of forced breathing. After another intraveneous administration of sodium heparin at the rate of 500 U/kg, 100 U/kg per hour, the dog was subjected to the following experiments.

(1) Intra-arterial administration

A glass cannula was cannulated to the left coronary artery through the right carotid so as to form an extracorporeal circulation path. The blood flow in coronary artery was measured by an electromagnetic blood flow meter equipped with a blood flow observation probe in the extracorporeal circulation path. A compound to be tested was administered by using a microsyringe through the branch prepared in the extracorporeal circulation path, and the increased amount of the blood flow in coronary artery was measured. Similarly, 30 micrograms or 100 micrograms of adenosin were administered and the increased amount of the blood flow in coronary artery was measured respectively, and the larger value among the measured data was considered as 100%, then the increased effect (%) of the blood flow in coronary artery caused by the test compound was calculated. The results are shown in Table 3 below.

(2) Intraveneous administration

Morawitz's cannula was cannulated to the coronary sinus venosus through the auricula dextra cordis, and the blood in vein was circulated to the right carotid. The blood flow was measured by an electromagnetic blood flow meter equipped with a blood flow observation probe in the extracorporeal circulation path of the vein. The systolic force was measured by a systolometer (pick-up) placed at the left ventricle of heart, the blood pressure was measured from the femoral artery, and the heart rate was measured from the pulse. A compound to be tested was administered through the cannula being cannulated in femoral vein. The increased amount of the blood flow in coronary artery after the administration of the test compound is shown in Table 4, also the change of blood pressure is shown in Table 5. In the Tables 3 to 5, the compounds to be tested were numbered similarly as those indicated in Tables 1 and 2.

TABLE 3

Increasing effect of blood flow in coronary artery (%)

| Test Compound No. | Dosage (micrograms) | | | | | |
|---|---|---|---|---|---|---|
| | 3 | 10 | 30 | 100 | 300 | 1000 |
| 1 | — | 28 | 95 | 123 | 133 | — |
| 2 | — | 8 | 33 | 125 | 183 | — |
| 3 | — | 6 | 13 | 40 | 53 | — |
| 4 | 22 | 65 | 96 | 107 | 117 | — |
| 5 | 13 | 24 | 67 | 85 | 98 | — |
| 6 | 11 | 24 | 55 | 87 | 108 | — |
| 7 | — | 6 | 12 | 22 | 110 | — |
| 8 | 7 | 7 | 41 | 90 | 110 | — |
| 9 | 19 | 54 | 88 | 95 | 85 | — |
| 10 | 2 | 6 | 23 | 42 | 78 | — |
| 11 | 10 | 21 | 32 | 56 | 75 | — |
| 12 | 6 | 25 | 52 | 60 | 76 | — |
| 13 | 32 | 59 | 75 | — | — | — |
| 14 | 2 | 11 | 28 | 64 | 100 | — |
| 15 | 4 | 35 | 71 | 87 | 88 | — |
| 16 | 27 | 61 | 105 | 119 | — | — |
| 17 | 18 | 28 | 75 | 95 | — | — |
| 19 | 38 | 47 | 83 | 71 | — | — |
| 21 | 12 | 31 | 72 | 93 | — | — |
| 23 | — | 6 | 63 | 136 | 141 | — |
| 24 | 9 | 75 | 192 | 239 | 225 | — |
| 25 | 28 | 106 | 244 | 269 | — | — |
| 26 | — | 8 | 56 | 300 | 386 | — |
| 27 | 6 | 53 | 178 | 128 | — | — |
| 28 | 12 | 44 | 89 | 94 | 74 | — |
| 29 | 25 | 164 | 181 | 170 | — | — |
| 30 | — | 20 | 145 | 175 | — | — |
| 31 | — | — | 18.8 | 31.2 | 62.5 | — |
| 32 | — | — | 9.2 | 30.8 | 64.6 | 93.8 |
| 33 | — | — | — | 10.8 | 43.1 | 83.1 |
| 34 | — | — | 5.7 | 21.4 | 62.9 | 92.9 |
| 35 | — | — | 3.8 | 26.9 | 63.5 | 105.8 |
| 36 | — | — | 5.3 | 30.7 | 74.7 | 100.0 |
| 37 | — | — | — | 6 | 31 | — |
| 38 | — | 9 | 47 | 188 | 252 | — |
| 39 | — | — | — | 3 | 33 | — |
| 40 | — | 5 | 29 | 68 | 112 | — |
| 41 | — | 6 | 20 | 31 | 109 | — |
| 42 | — | 5 | 80 | 120 | 146 | — |

TABLE 4

Increased amount of the blood flow in coronary artery (ml/min.)

| Test Compound No. | Dosage (micrograms/kg) | | | | | |
|---|---|---|---|---|---|---|
| | 3 | 10 | 30 | 100 | 300 | 1000 |
| 1 | 4 | 34 | 63 | 62 | 42 | — |
| 2 | — | 3 | 13 | 38 | 52 | — |
| 3 | 2 | 1 | 3 | 14 | 38 | — |
| 4 | 3 | 8 | 22 | 62 | 90 | — |
| 5 | 3 | 12 | 47 | 89 | 77 | — |
| 6 | — | 3 | 25 | 58 | 64 | — |
| 7 | — | — | 1 | 15 | 47 | — |
| 8 | — | 1 | 2 | 12 | 56 | — |
| 9 | 4 | 17 | 47 | 66 | 81 | — |
| 10 | — | 2 | 5 | 23 | 43 | — |
| 11 | 7 | 26 | 58 | 56 | 73 | — |
| 12 | 5 | 30 | 74 | 63 | — | — |
| 31 | — | — | — | 6 | 32 | 61 |
| 32 | — | — | — | 16 | 55 | 97 |
| 33 | — | — | — | 1 | 4 | 48 |
| 34 | — | — | — | 22 | 47 | 54 |
| 35 | — | — | — | 5 | 17 | 47 |
| 36 | — | — | — | 4 | 12 | 38 |

TABLE 5

| Test Compound No. | Change of blood pressure Dosage (micrograms/kg) | | | | |
|---|---|---|---|---|---|
| | 3 | 10 | 30 | 100 | 300 |
| 1 | −6 | −17 | −36 | −42 | −46 |
| 2 | — | −2 | −6 | −21 | −34 |
| 3 | — | −1 | −4 | −18 | −34 |
| 4 | −5 | −15 | −25 | −34 | −51 |
| 6 | −3 | −5 | −15 | −32 | −44 |
| 7 | — | −2 | −4 | −9 | −14 |
| 8 | — | — | −3 | −16 | −33 |
| 9 | −14 | −28 | −36 | −41 | −36 |
| 10 | — | −5 | −9 | −13 | −34 |
| 11 | −5 | −18 | −33 | −41 | −48 |
| 12 | — | −5 | −23 | −49 | — |
| 13 | −7 | −16 | −32 | −52 | — |
| 14 | — | — | −2 | −14 | −32 |
| 15 | — | — | −3 | −9 | −27 |
| 16 | −3 | −12 | −27 | −42 | −54 |
| 17 | — | −4 | −14 | −55 | −76 |
| 18 | — | −5 | −19 | −33 | −43 |
| 19 | −22 | −34 | −44 | −55 | — |
| 20 | — | — | −4 | −8 | −32 |
| 21 | — | −7 | −12 | −28 | −42 |
| 22 | — | −2 | −8 | −18 | −36 |
| 24 | — | −6 | −18 | −30 | −44 |
| 25 | −9 | −34 | −46 | — | — |
| 26 | — | −6 | −10 | −21 | −42 |
| 27 | −4 | −10 | −27 | −52 | — |
| 28 | −1 | −10 | −7 | −20 | −47 |
| 29 | −7 | −23 | −45 | −70 | −80 |
| 30 | — | −1 | −16 | −38 | — |
| 31 | — | −1 | −4 | −8 | −23 |
| 32 | — | −1 | −6 | −8 | −19 |
| 35 | — | −4 | −6 | −9 | −26 |
| 37 | — | — | −1 | −5 | −18 |
| 38 | — | −2 | −10 | −35 | −57 |
| 43 | — | — | −4 | −16 | −23 |
| 44 | — | −1 | −3 | −6 | −52 |

REFERENCE EXAMPLE 1

4.2 Grams of potassium hydroxide were dissolved in 200 ml of methanol, then 10 g of 5-hydroxy-3,4-dihydrocarbostyril were added thereto. Next, 10 g of 2-bromoethanol were added dropwise thereto under refluxing conditions. The reaction mixture was further refluxed for 4 hours, then was concentrated. To the residue thus obtained was added water, and the insoluble matter was collected by filtration, and was washed with water, then recrystallized from methanol to yield 2.1 g of 5-(2-hydroxyethoxy)-3,4-dihydrocarbostyril in the form of colorless needle-like crystals. Melting point: 176°–178° C.

By a method similar to that described above, that were prepared compounds as follows:

5-(3-Hydroxypropoxy)-8-propenyloxy-3,4-dihydrocarbostyril

Colorless needle-like crystals (from chloroformhexane).

Melting point: 80.0°–81.5° C.

6-(2-Hydroxyethoxy)-3,4-dihydrocarbostyril

Colorless needle-like crystals (water-containing methanol).

Melting point: 153°–155° C.

6-(4-Hydroxybutoxy)-3,4-dihydrocarbostyril

Colorless needle-like crystals.

Melting point: 132°–133° C.

REFERENCE EXAMPLE 2

2 Grams of 5-(2-hydroxyethoxy)-3,4-dihydrocarbostyril and 2 ml of triethylamine were added to 50 ml of chloroform, then 1 g of diketene was added dropwise thereto, and the whole reaction mixture was stirred at room temperature for 2 days. The insoluble matter formed in the reaction mixture was removed by filtration, and the filtrate was concentrated, then the residue obtained was purified by silica gel column chromatography (eluant: chloroform), the eluate obtained was concentrated and the residue was recrystallized from chloroform-ether to yield 1.5 g of 5-(2-acetoacetoxyethoxy)-3,4-dihydrocarbostyril in the form of colorless needle-like crystals. Melting point: 134.5°–135.5° C.

By a method similar to that described above, there was prepared 5-(3-acetoacetoxypropoxy)-8-propenyloxy-3,4-dihydrocarbostyril in the form of colorless powdery crystals (from chloroform-hexane). Melting point: 66°–67° C.

REFERENCE EXAMPLE 3

Into 30 ml of ethanol, 2 g of 6-(2-acetoacetoxy)-3,4-dihydrocarbostyril and 1 g of 3-nitrobenzaldehyde were added, then 0.1 ml of piperidine was added to the reaction mixture under an ice-cooled condition. The reaction was continued for 3 days at room temperature under stirring. Then the reaction mixture was concentrated, then ether was added thereto, and the precipitate formed was collected by filtration, then recrystallized from chloroform-ether to yield 1.3 g of 6-{2-[2-(3-nitrobenzyliden)acetoacetoxy]ethoxy}-3,4-dihydrocarbostyril in the form of light yellowish powdery crystals.

NMR: $\delta(CDCl_3)$=2.45 (3H, s), 2.46–2.70 (2H, m), 2.75–3.00 (2H, m), 4.00–4.27 (2H, m), 4.47–4.65 (2H, m), 6.50–6.70 (3H, m), 7.25–7.70 (3H, m), 7.95–8.30 (3H, m).

REFERENCE EXAMPLE 4

10 Grams of 3-nitrobenzaldehyde and 11 g of 2-chloroethyl acetoacetate were dissolved in 100 ml of toluene, then hydrogen chloride gas was introduced to the solution under an ice-cooled condition. The reaction mixture was allowed to stand for 2 days at room temperature, and the mixture was concentrated. The residue obtained was extracted with chloroform, and the chloroform layer was washed with a saturated sodium chloride aqueous solution, and a saturated sodium hydrogencarbonate aqueous solution, then dried with anhydrous magnesium sulfate. Chloroform was removed by distillation, then the residue obtained was recrystallized from isopropanol to yield 10 g of 2-chloroethyl 2-(3-nitrobenzylyden)acetoacetate in the form of colorless needle-like crystals.

Melting point: 95°–97° C.

REFERENCE EXAMPLE 5

25 Grams of 3-chloropropyl 2-(3-nitrobenzyliden)acetoacetate which was prepared by a method similar to that described in Reference Example 3, and 10 g of methyl 3-aminocrotonate were added to 100 ml of methanol, and the mixture was refluxed for 4 hours, then allowed to stand to cool overnight. The crystals precipitated were collected by filtration, recrystallized from isopropanol to yield 22.7 g of 3-chloropropyl methyl 1,4dihydro-2,6-dimethyl-4-(3-nitrophenyl)pyridine-3,5-dicarboxylate in the form of yellowish prism-like crystals. Melting point: 144°–145° C.

REFERENCE EXAMPLE 6

13.2 Grams of o-trifluoromethylbenzaldehyde, 14.6 g of 4-chlorobutyl acetoacetate and 8.8 g of methyl 3-aminocrotonate were added to 50 ml of isopropanol, and the whole mixture was refluxed by heating for 4 hours. The reaction mixture was concentrated, and the residue was purified by a silica gel column chromatography (eluant=chloroform) to yield 18.2 g of 4-chlorobutyl methyl 1,4-dihydro-2,6-dimethyl-4-(2-trifluoromethylphenyl)pyridine-3,5-dicarboxylate in the form of yellow oily substance.

NMR: (CDCl$_3$)δ; 1.47–1.87 (4H, m), 2.23 (6H, d, J=2 Hz), 3.23–3.50 (2H, m), 3.50 (3H, s), 3.80–4.20 (2H, m), 5.37–5.53 (1H, m), 5.70 (1H, brs), 6.97–7.60 (4H, m).

REFERENCE EXAMPLE 7

2.8 Grams of metallic magnesium, 25 g of 2-bromo-α,α,α-trifluorotoluene and 120 ml of ether were reacted to prepare a Grignard ragent by a conventional method, then 15 g of N-methylformanilide were added dropwise thereto, and the reaction mixture was allowed to stand for 3 hours. Under an ice-cooled condition, a dilute sulfuric acid was added to the reaction mixture. The ethereal layer was separated and was washed with a saturated sodium chloride aqueous solution and with a saturated sodium hydrogencarbonate aqueous solution, then was dried with anhydrous sodium sulfate, and was concentrated. The residue was purified by distillation under reduced pressure to yield 13.2 g of 2-trifluoromethylbenzaldehyde. Boiling point: 62°–65° C. (at 17 mm-Hg).

REFERENCE EXAMPLE 8

18 Grams of 2-methylmercaptobenzyl chloride and 30 g of hexamine were added to 200 ml of chloroform and the mixture was refluxed for 2 hours. Then the reaction mixture was concentrated, and the residue obtained was refluxed with 100 ml of 20%-hydrochloric acid for 2 hours. After being cooled, the reaction mixture was extracted with chloroform, and the chloroform layer was washed with a saturated sodium chloride aqueous solution and with a saturated sodium hydrogencarbonate aqueous solution, then concentrated. The product was purified by distillation under reduced pressure to obtain 9.00 g of 2-methylmercaptobenzaldehyde. Boiling point: 143°–147° C. (at 15 mm-Hg).

REFERENCE EXAMPLE 9

6 Grams of 2-formylbenzoic acid and 6 g of potassium carbonate were added to 30 ml of dimethylformamide, then 6 g of methyl iodide were added dropwise thereto at room temperature with stirring. The reaction mixture was continuously stirred at room temperature overnight, then was concentrated. The residue obtained was extracted with chloroform, and the chloroform layer was washed with water, and was dried with anhydrous magnesium sulfate, then concentrated. The residue obtained was purified by distillation under reduced pressure to yield 3 g of methyl 2-formylbenzoate. Boiling point: 95° C. (at 0.5 mm-Hg).

REFERENCE EXAMPLE 10

3 Grams of methyl 1,4-dihydro-2,6-dimethyl-4-(3-nitrophenyl)pyridin-3-carboxy-5-carboxylate were dissolved in 10 ml of hexamethylphosphoramide and 1.2 ml of 30%—sodium hydroxide aqueous solution, then 1.4 ml of epibromohydrin were added thereto and the mixture was stirred at room temperature overnight. To the reaction mixture was added water and the mixture was extracted with ethyl acetate. The organic layer was washed with water, dried, then the solvent was removed by distillation, and the residue obtained was crystallized from diethyl ether to yield 2.6 g of methyl β,α-epoxypropyl 2,6-dimethyl-4-(3-nitrophenyl)-1,4-dihydropyridin-3,5-dicarboxylate.

REFERENCE EXAMPLE 11

10 Grams of 3-nitrobenzaldehyde and 11 g of 2-chloroethyl acetoacetate were dissolved in 100 ml of toluene, then under an ice-cooled condition, hydrogen chloride gas was introduced into the solution for 2 hours. The reaction mixture was allowed to stand at room temperature for 2 days, and was concentrated. The residue obtained was extracted with chloroform, then the chloroform layer was washed with a saturated sodium chloride aqueous solution and with a saturated sodium hydrogen carbonate aqueous solution and dried with anhydrous magnesium sulfate. Chloroform was removed by distillation and the residue was recrystallized from isopropanol to yield 10 g of 2-chloroethyl 2-(3-nitrobenzyliden)acetoacetate in the form of colorless needle-like crystals.

Melting point: 95°–97° C.

REFERENCE EXAMPLE 12

25 Grams of 2-chloroethyl 2-(3-nitrobenzyliden)acetoacetate which was prepared by a method similar to that described in Reference Example 11, and 10 g of methyl 3-aminocrotonate were added to 100 ml of methanol and the whole mixture was refluxed for 4 hours, then allowed to stand overnight. The precipitates formed were collected by filtration, and were recrystallized from isopropanol to yield 22.7 g of 2-chloroethyl methyl 1,4-dihydro-2,6-dimethyl-4-(3-nitrophenyl)pyridin-3,5-dicarboxylate in the form of yellowish prism-like crystals. Melting Point: 144°–145° C.

REFERENCE EXAMPLE 13

4 Grams of 2-chloroethyl methyl 1,4-dihydro-2,6-dimethyl-4-(3-nitrophenyl)pyridin-3,5-dicarboxylate and 6 ml of cyclohexylamine were added to 70 ml of toluene and the mixture was refluxed for 10 hours. After cooling the reaction mixture, the precipitates thus formed were removed by filtration, the filtrate was concentrated, and the residue was extracted with chloroform. The chloroform layer was washed with 5%-hydrochloric acid aqueous solution, 2%-sodium hydroxide aqueous solution and a saturated sodium chloride aqueous solution, and dried with anhydrous magnesium sulfate, then was concentrated. The concentrate was purified by a silica gel column chromatography (eluant: chloroform/methanol=20/1) to yield 1.0 g of N-cyclohexylaminoethyl methyl 1,4-dihydro-2,6-dimethyl-4-(3-nitrophenyl)methyl 1,4-dihydro-2,6-dimethyl-4-(3-nitrophenyl)pyridin-3,5-dicarboxylate in the form of yellowish needle-like crystals. Melting point: 84°–87° C.

REFERENCE EXAMPLE 14

To 100 ml of dimethylformamide, there were added 7.45 g of N-cyclohexyl-N-(2-hydroxyethyl)-4-(6-carbostyriloxy)butyramide and 0.5 ml of triethylamine, then the whole mixture was heated at 80° to 90° C. on an oil bath. Next, 1.8 g of diketene were added dropwise to the reaction mixture, then the mixture was stirred for 1 hour at the same temperature. The reaction mixture was concentrated then was purified by a silica gel column chromatography (eluant: chloroform/methanol=50/1), and the solvent was removed by distillation under reduced pressure to yield 6.33 g of N-(2- acetoacetoxyethyl)N-cyclohexyl-4-(6-carbostyriloxy)-butyramide in the form of a brownish oily substance.

NMR (CDCl$_3$)δ (ppm) 0.8–1.9 (10H, m), 1.95–2.35 (2H, m), 2.20 (3H, s), 2.40–2.67 (2H, m); 3.33 (2H, s), 3.40 (2H, t, J=6.6 Hz), 3.40–3.70 (1H, m), 3.97 (2H, t, J=6.5 Hz), 4.13 (2H, t, J=6.6 Hz), 6.60 (1H, d, J=9.6 Hz), 6.89 (1H, d, J=2 Hz), 7.03 (1H, dd, J$_1$=9.0 Hz, J$_2$=2 Hz), 1.27 (1H, d, J=9.0 Hz), 7.60 (1H, d, J=9.6 Hz), 12.5 (1H, bs).

REFERENCE EXAMPLE 15

To 10 ml of pyridine were added 0.9 g of 3-nitrobenzaldehyde and 2.7 g of N-(2-acetoacetoxyethyl)-N-cyclohexyl-4-(6-carbostyriloxy)butyramide, and the mixture was heated at 90°–100° C. for 20 hours. After cooling the reaction mixture was extracted with chloroform, and the chloroform layer was washed with a saturated aqueous solution of potassium hydrogensulfate and with a saturated aqueous solution of sodium chloride, then was dried with anhydrous magnesium sulfate. After being concentrated, the residue was purified by a silica gen column chromatography (eluant: chloroform/methanol=100/1), then the eluate was dried under vacuum condition to yield 0.2 g of N-{2-[2-(3-nitrobenzyliden)acetoacetoxy]ethyl}-N-cyclohexyl-4-(6-carbostyriloxy)butyramide in the form a brown oily substance.

NMR (CDCl$_3$)δ (ppm) 0.8–1.9 (10H, m), 1.95–2.35 (2H, m), 2.40–2.67 (2H, m), 2.43 (3H, s), 3.45 (2H, t, J=6.5 Hz), 3.40–3.70 (1H, m), 3.97 (2H, t, J=6.5 Hz), 4.33 (2H, t, J-6.5 Hz), 6.60 (1H, d, J=9.6 Hz), 6.89 (1H, d, J-2.0 Hz), 7.03 (1H, dd, J$_1$=9.0 Hz, J$_2$=2 Hz), 7.27 (1H, d, J=9.0 Hz), 7.50 (1H, s), 7.45–7.83 (3H, m), 8.10–8.33 (2H, m), 12.5 (1H, bs).

REFERENCE EXAMPLE 16

1 Gram of 2-cyclohexlaminoethyl methyl 1,4-dihydro-2,6-dimethyl-4-(3-nitrophenyl)pyridin-3,5-dicarboxylate was added to 20 ml of acetone, then 0.34 g of potassium carbonate and 1 ml of water were added thereto. Under an ice-cooled condition with stirring, an acetone solution containing 0.35 g of 4-chlorobutyl chloride was added dropwise thereto, then the reaction mixture was stirred under an ice-cooled condition for 1 hour, and further stirred at room temperature for 3 hours. The reaction mixture was concentrated, and the residue was extracted with chloroform, then the chloroform layer was washed with 0.5N-sodium hydroxide aqueous solution, then with a saturated sodium chloride aqueous solution, and dried with anhydrous magnesium sulfate. The dried chloroform extract was concentrated and the residue obtained was purified by a silica gel column chromatography (eluant: chloroform), then the eluate was dried under vacuum to yield 0.5 g of 2-[N-(4-chlorobutyl)-N-cyclohexyl]aminoethyl methyl 1,4-dihydro-2,6-dimethyl-4-(3-nitrophenyl)pyridin-3,5-dicarboxylate in the form a yellowish oily substance.

NMR (CDCl$_3$)δ (ppm) 0.8–1.90 (10H, m), 1.90–2.20 (2H, m), 2.27 (6H, s), 2.40 (2H, t, J=6.0 Hz), 3.20–3.70 (5H, m), 3.55 (3H, s), 4.03 (2H, t, J-6.9 Hz), 5.00 (1H, s), 6.65 (1H, bs), 7.25 (1H, t, J=7.2 Hz), 7.53 (1H, dd, J$_1$=7.2 Hz, J$_2$=2.0 Hz), 7.87 (1H, dd, J$_1$=7.2 Hz, J$_2$=2.0 Hz), 7.98 (1H, t, J=2.0 Hz).

EXAMPLE 1

1.6 Grams of 8-hydroxy-3,4-dihydrocarbostyril and 1.5 g of potassium carbonate were added to 30 ml of dimethylformamide, then this mixture was heated to 80°–90° C., and 30 ml of dimethylformamide solution containing 5 g of 3-iodopropylmethyl 1,4-dihydro-2,6-dimethyl-4-(3-nitrophenyl)pyridin-3,5-dicarboxylate were added dropwise thereto. The reaction mixture was stirred at the same temperature for 5 hours, and the reaction mixture was concentrated, then the residue obtained was extracted with chloroform, the chloroform layer was washed with water, 0.5N-sodium hydroxide aqueous solution, 5%-hydrochloric acid aqueous solution and a saturated sodium chloride aqueous solution, then was dried with anhydrous magnesium sulfate. The dried chloroform extract was concentrated and purified by a silica gel column chromatography (eluant: chloroform/methanol=100/1). The eluate was recrystallized from methanol containing water to yield 2.9 g of 8-{3-[2,6-dimethyl-5-methoxycarbonyl-4-(3-nitrophenyl)-1,4-dihydropyridin-3-carboxy]propoxy}-3,4-dihydrocarbostyril in the form of yellowish plate-like crystals.

Melting point: 167°–167.5° C.

EXAMPLES 2–48

By a method similar to that described in Example 1, there were prepared compounds represented by the following general formula as shown in Table 6 below.

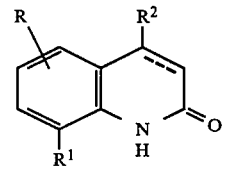

wherein R is a side-chain of the formula,

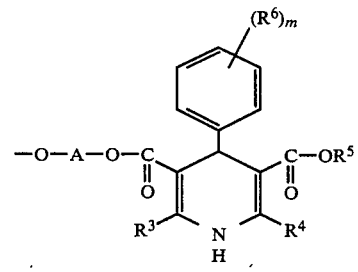

TABLE 6

| Example No. | Substituted position of the side-chain or R | R | R$^1$ | R$^2$ | R$^3$ | R$^4$ | R$^5$ | (R$^6$)$_m$ |
|---|---|---|---|---|---|---|---|---|
| 2 | 5 | Side-chain | H | H | CH$_3$ | CH$_3$ | CH$_3$ | 3-NO$_2$ |
| 3 | 5 | Side-chain | —OCH$_2$CH=CH$_2$ | H | CH$_3$ | CH$_3$ | CH$_3$ | 3-NO$_2$ |
| 4 | 6 | Side-chain | H | H | CH$_3$ | CH$_3$ | CH$_3$ | 3-NO$_2$ |
| 5 | 7 | Side-chain | H | H | CH$_3$ | CH$_3$ | CH$_3$ | 3-NO$_2$ |

TABLE 6-continued

| | | | | | | | | |
|---|---|---|---|---|---|---|---|---|
| 6 | 8 | H | Side-chain | H | $CH_3$ | $CH_3$ | $CH_3$ | 3-$NO_2$ |
| 7 | 4 | H | H | Side-chain | $CH_3$ | $CH_3$ | $CH_3$ | 3-$NO_2$ |
| 8 | 5 | Side-chain | H | H | $CH_3$ | $CH_3$ | $CH_3$ | 3-$NO_2$ |
| 9 | 5 | Side-chain | $-OCH_2C\equiv CH$ | H | $CH_3$ | $CH_3$ | $CH_3$ | 3-$NO_2$ |
| 10 | 5 | Side-chain | $-O(CH_2)_2CH_3$ | H | $CH_3$ | $CH_3$ | $CH_3$ | 3-$NO_2$ |
| 11 | 4 | H | H | Side-chain | $CH_3$ | $CH_3$ | $CH_3$ | 3-$NO_2$ |
| 12 | 6 | Side-chain | H | $CH_3$ | $CH_3$ | $CH_3$ | $CH_3$ | 3-$NO_2$ |
| 13 | 5 | Side-chain | H | H | $CH_3$ | $CH_3$ | $CH_3$ | 3-$NO_2$ |
| 14 | 5 | Side-chain | H | H | $CH_3$ | $CH_3$ | $CH_3$ | 3-$NO_2$ |
| 15 | 5 | Side-chain | $-OCH_2CH=CH_2$ | H | $CH_3$ | $CH_3$ | $CH_3$ | 3-$NO_2$ |
| 16 | 6 | Side-chain | H | H | $CH_3$ | $CH_3$ | $CH_3$ | 3-$NO_2$ |
| 17 | 6 | Side-chain | H | H | $CH_3$ | $CH_3$ | $CH_3$ | 3-$NO_2$ |
| 18 | 6 | Side-chain | H | H | $CH_3$ | $CH_3$ | $CH_3$ | 2-$NO_2$ |
| 19 | 6 | Side-chain | H | H | $CH_3$ | $CH_3$ | $CH_3$ | 2-$NO_2$ |
| 20 | 6 | Side-chain | H | H | $CH_3$ | $CH_3$ | $CH_3$ | 2-$NO_2$ |
| 21 | 6 | Side-chain | H | H | $CH_3$ | $CH_3$ | $CH_3$ | 2-$NO_2$ |
| 22 | 6 | Side-chain | H | H | $CH_3$ | $CH_3$ | $CH_3$ | 2-$NO_2$ |
| 23 | 6 | Side-chain | H | H | $CH_3$ | $CH_3$ | $CH_3$ | 2-$NO_2$ |
| 24 | 5 | Side-chain | $-OCH_2CH=CH_2$ | H | $CH_3$ | $CH_3$ | $CH_3$ | 3-$NO_2$ |
| 25 | 5 | Side-chain | H | H | $CH_3$ | $CH_3$ | $CH_3$ | 3-$NO_2$ |
| 26 | 6 | Side-chain | H | H | $CH_3$ | $CH_3$ | $CH_3$ | 3-$NO_2$ |
| 27 | 5 | Side-chain | H | H | $CH_3$ | $CH_3$ | $CH_3$ | 3-$NO_2$ |
| 28 | 6 | Side-chain | H | H | $CH_3$ | $CH_3$ | $CH_3$ | 3-$NO_2$ |
| 29 | 7 | Side-chain | H | H | $CH_3$ | $CH_3$ | $CH_3$ | 3-$NO_2$ |
| 30 | 5 | Side-chain | —2-Tetrahydropyranyloxy | H | $CH_3$ | $CH_3$ | $CH_3$ | 3-$NO_2$ |
| 31 | 5 | Side-chain | —OH | H | $CH_3$ | $CH_3$ | $CH_3$ | 3-$NO_2$ |
| 32 | 6 | Side-chain | H | H | $CH_3$ | $CH_3$ | $CH_3$ | 3-$NO_2$ |
| 33 | 8 | H | Side-chain | H | $CH_3$ | $CH_3$ | $CH_3$ | 3-$NO_2$ |
| 34 | 6 | Side-chain | H | H | $CH_3$ | $CH_3$ | $CH_3$ | 3-$NO_2$ |
| 35 | 6 | Side-chain | H | H | $CH_3$ | $CH_3$ | $CH_3$ | 3-$NO_2$ |
| 36 | 6 | Side-chain | H | H | $CH_3$ | $CH_3$ | $CH_3$ | 3-$NO_2$ |
| 37 | 6 | Side-chain | H | H | $CH_3$ | $CH_3$ | $CH_3$ | 3-$NO_2$ |
| 38 | 6 | Side-chain | H | H | $CH_3$ | $CH_3$ | $CH_3$ | 2-$CF_3$ |
| 39 | 6 | Side-chain | H | H | $CH_3$ | $CH_3$ | $CH_3$ | 2-$CF_3$ |
| 40 | 6 | Side-chain | H | H | $CH_3$ | $CH_3$ | $CH_3$ | 2-$SCH_3$ |
| 41 | 6 | Side-chain | H | H | $CH_3$ | $CH_3$ | $CH_3$ | 2-Cl |
| 42 | 6 | Side-chain | H | H | $CH_3$ | $CH_3$ | $CH_3$ | H |
| 43 | 6 | Side-chain | H | H | $CH_3$ | $CH_3$ | $CH_3$ | 2-$CH_3$ |
| 44 | 6 | Side-chain | H | H | $CH_3$ | $CH_3$ | $CH_3$ | 2,4-$(Cl)_2$ |
| 45 | 6 | Side-chain | H | H | $CH_3$ | $CH_3$ | $CH_3$ | 3,4-$(OCH_3)_2$ |
| 46 | 6 | Side-chain | H | H | $CH_3$ | $CH_3$ | $CH_3$ | 3,4,5-$(OCH_3)_3$ |
| 47 | 6 | Side-chain | H | H | $CH_3$ | $CH_3$ | $CH_3$ | 2-$COOCH_3$ |
| 48 | 6 | Side-chain | H | H | $CH_3$ | $CH_3$ | $CH_3$ | H |

| Example No. | A | Carbon-carbon bond between 3- and 4- positions | Crystal form (Recrystallization solvent) | Melting point (°C.) |
|---|---|---|---|---|
| 2 | $-(CH_2)_2-$ | Double bond | Light yellowish powdery crystals (Dimethylformamide-methanol) | 271–272 |
| 3 | $-(CH_2)_2-$ | Single bond | Yellowish needle-like crystals (Methanol) | 135–137 |
| 4 | $-(CH_2)_2-$ | Double bond | Light yellowish powdery crystals (Dimethylformamide-methanol) | 246–249 |
| 5 | $-(CH_2)_2-$ | Single bond | Yellowish prism-like crystals (Methanol) | 178–180 |
| 6 | $-(CH_2)_2-$ | Single bond | Light yellowish needle-like crystals (Water-containing methanol) | 176–177 |
| 7 | $-(CH_2)_2-$ | Double bond | Yellowish needle-like crystals (Methanol) | 169–171 |
| 8 | $-(CH_2)_3-$ | Double bond | Light yellowish powdery crystals (Dimethylformamide-methanol) | 244–245 |
| 9 | $-(CH_2)_3-$ | Single bond | Yellowish prism-like crystals (Methanol) | 183.5–184.5 |
| 10 | $-(CH_2)_3-$ | Single bond | Light yellowish prism-like crystals (Methanol) | 150.5–152 |
| 11 | $-(CH_2)_3-$ | Double bond | Light yellowish powdery crystals (Water-containing methanol) | 148–149.5 |
| 12 | $-(CH_2)_3-$ | Double bond | Light yellowish powdery crystals (Dimethylformamide-methanol) | 211–212 |
| 13 | $-(CH_2)_4-$ | Single bond | Light yellowish powdery crystals (Dimethylformamide-methanol) | 246–248 |
| 14 | $-(CH_2)_4-$ | Double bond | Light yellowish powdery crystals (Dimethylformamide-methanol) | 252–254 |
| 15 | $-(CH_2)_4-$ | Single bond | Yellowish powdery crystals (Methanol) | 168–169.5 |
| 16 | $-(CH_2)_4-$ | Single bond | Light yellowish powdery crystals (Chloroform-methanol) | 153–155 |
| 17 | $-(CH_2)_4-$ | Double bond | Yellow-orange powdery crystals (Chloroform-methanol) | 229–230.5 |
| 18 | $-(CH_2)_2-$ | Double bond | Yellowish powdery crystals | 255–258 |

TABLE 6-continued

| | | | | |
|---|---|---|---|---|
| | | | (Dimethylformamide-methanol) | |
| 19 | —(CH$_2$)$_3$— | Double bond | Yellowish powdery crystals (Dimethylformamide-methanol) | 246–247 |
| 20 | —(CH$_2$)$_4$— | Double bond | Yellowish powdery crystals (Dimethylformamide-methanol) | 222–224 |
| 21 | —(CH$_2$)$_2$— | Single bond | Yellowish powdery crystals (Dimethylformamide-methanol) | 235–236 |
| 22 | —(CH$_2$)$_3$— | Single bond | Yellowish prism-like crystals (Methanol) | 182–184 |
| 23 | —(CH$_2$)$_4$— | Single bond | Yellowish needle-like crystals (Methanol) | 152–154 |
| 24 | —(CH$_2$)$_3$— | Single bond | Yellowish powdery crystals (Chloroform-n-hexane) | 156–157.5 |
| 25 | —(CH$_2$)$_2$— | Single bond | Yellowish powdery crystals (Chloroform-isopropyl ether) | 262–263.5 |
| 26 | —(CH$_2$)$_2$— | Single bond | Light yellowish powdery crystals (Chloroform-ether) | 172.5–174 |
| 27 | —(CH$_2$)$_3$— | Single bond | Yellowish prism-like crystals (Methanol) | 173–176 |
| 28 | —(CH$_2$)$_3$— | Single bond | Light yellowish needle-like crystals (Methanol) | 180–181 |
| 29 | —(CH$_2$)$_3$— | Single bond | Light yellowish powdery crystals (Water-containing methanol) | 137–139 |
| 30 | —(CH$_2$)$_3$— | Single bond | Yellow-brown oily substance | NMR$^1$ (cf. Note 1) |
| 31 | —(CH$_2$)$_3$— | Single bond | Yellowish prism-like crystals (Water-containing methanol) | 193.5–194 |
| 32 | —(CH$_2$)$_3$— | Double bond | Light brownish powdery crystals (Water-containing methanol) | 227–227.5 |
| 33 | —(CH$_2$)$_3$— | Single bond | Yellowish plate-like crystals (Water-containing methanol) | 167–167.5 |
| 34 | —CH$_2$CH(OH)CH$_2$— | Single bond | Yellowish powdery substance (Chloroform-isopropyl ether) | NMR$^2$ & IR data-1 (cf. Note 2) |
| 35 | —CH$_2$CH(OAc)CH$_2$— | Single bond | Yellowish powdery substance (Chloroform-isopropyl ether) | NMR$^3$ & IR data-2 (cf. Note 3) |
| 36 | —CH$_2$CH(OH)CH$_2$— | Double bond | Yellowish powdery substance (Isopropanol-isopropyl ether) | NMR$^4$ & IR data-3 (cf. Note 4) |
| 37 | —CH$_2$CH(OAc)CH$_2$— | Double bond | Yellowish powdery substance (Chloroform-isopropyl ether) | NMR$^5$ & IR data-4 (cf. Note 5) |
| 38 | —(CH$_2$)$_4$— | Double bond | Colorless needle-like crystals (Methanol) | 138–141 |
| 39 | —(CH$_2$)$_4$— | Single bond | Colorless needle-like crystals (Methanol) | 103–105 |
| 40 | —(CH$_2$)$_4$— | Single bond | Light yellowish needle-like crystals (Water-containing methanol) | 90–92 |
| 41 | —(CH$_2$)$_4$— | Single bond | Light yellowish amorphous crystals (Methanol) | 135 |
| 42 | —(CH$_2$)$_4$— | Single bond | Colorless flake-like crystals (Methanol) | 119 |
| 43 | —(CH$_2$)$_4$— | Single bond | Colorless amorphous crystals (Methanol) | 93–95 |
| 44 | —(CH$_2$)$_4$— | Single bond | Light yellowish amorphous crystals (Methanol) | 138.5–140 |
| 45 | —(CH$_2$)$_4$— | Single bond | Colorless amorphous crystals (Methanol) | 149–150 |
| 46 | —(CH$_2$)$_4$— | Single bond | Colorless amorphous crystals (Methanol) | 121–123 |
| 47 | —(CH$_2$)$_4$— | Single bond | Light yellowish amorphous crystals (Methanol) | 178–181 |
| 48 | —(CH$_2$)$_3$— | Single bond | Colorless amorphous crystals | 218–220 |

TABLE 6-continued (Methanol)

Note 1:
NMR[1] δ (in CDCl$_3$) 1.30–21.5 (8H, m), 2.30 (6H, s), 2.33–2.55 (2H, m), 2.70–3.00 (2H, m), 3.23 (2H, t, J=7Hz), 3.53 (3H, s), 3.75 (2H, t, J=6.5Hz), 4.03 (2H, t, J=7Hz), 4.10–4.30 (1H, m), 5.00 (1H, s), 6.10 (1H, bs), 6.20 (1H, d, J=9Hz), 6.83 (1H, d, J=9Hz), 7.10–8.05 (5H, m)
Note 2:
NMR[2] δ (in CDCl$_3$) 2.25 (3H, s), 2.29 (3H, s), 2.30–2.90 (4H, m), 3.53 (3H, s), 3.50–3.90 (2H, m), 3.90–4.30 (3H, m), 5.00 (1H, s), 6.50 (3H, bs), 6.70 (1H, bs), 7.00–8.00 (4H, m), 8.81 (1H, bs)
IR data-1 $\nu_{KBr}$ cm$^{-1}$: 3340 (M), 3100 (W), 2950 (W), 1690 (SH), 1680 (S), 1630 (SH), 1530 (S), 1510 (S), 1350 (S)
Note 3:
NMR[3] δ (in CDCl$_3$) 2.00 (3H, s), 2.27 (3H, s), 2.30 (3H, s), 2.50 (2H, t, J=7Hz), 8.84 (2H, t, J—7Hz), 3.89 (3H, s), 3.83 (2H, t, J=6Hz), 4.23 (2H, t, J=5Hz), 5.00 (1H, s), 5.10–5.30 (1H, m), 6.40–6.70 (3H, m), 6.74 (1H, bs), 7.10–8.00 (4H, m), 8.96 (1H, bs)
IR data-2 $\nu_{KBr}$ cm$^{-1}$: 3350 (M), 3100 (W), 2980 (W), 2960 (W), 1745 (M), 1690 (S), 1680 (S), 1630 (SH), 1530 (S), 1510 (S), 1350 (S)
Note 4:
NMR[4] δ (in CDCl$_3$) 2.25 (3H, s), 2.27 (3H, s), 3.47 (3H, s), 3.70–4.10 (5H, m), 4.93 (1H, s), 6.41 (1H, d, J=9Hz), 6.90–8.00 (8H, m), 8.97 (1H, bs)
IR data-3 $\nu_{KBr}$ cm$^{-1}$: 3350 (M), 3100 (W), 2980 (W), 1690 (SH), 1660 (S), 1620 (S), 1530 (S), 1350 (S)
Note 5:
NMR[5] δ (in CDCl$_3$) 2.27, 2.30 (3H, each s), 2.27 (3H, s), 2.30 (3H, s), 3.55 (3H, s), 3.90 (2H, t, J=5Hz), 4.25 (2H, t, J—5Hz), 5.97 (1H, s), 5.10–5.30 (1H, m), 6.35 (1H, bs), 6.61 (1H, d, J=9Hz), 6.70–8.00 (8H, m), 12.33 (1H, bs)
IR data-4 $\nu_{KBr}$ cm$^{-1}$: 3340 (W), 3100 (W), 2980 (W), 1745 (M), 2690 (SH), 1670 (S), 1635 (S), 1530 (S), 1350 (S)

EXAMPLE 49

2.0 Grams of 5-(2-hydroxyethoxy)-3,4-dihydrocarbostyril, 3.3 g of 5-methoxycarbonyl-2,6-dimethyl-4-(3-nitrophenyl)-1,4-dihydropyridin-3-carboxylic acid and 2.1 g of dicyclohexylcarbodiimide were added to 50 ml of dimethylformamide, and the mixture was heated at 80°–90° C. for 5 hours. After cooling the reaction mixture, the precipitate was removed by filtration, and the filtrate was concentrated, then the residue was extracted with chloroform. The chloroform layer was washed with 1N-sodium hydroxyde aqueous solution and with a saturated sodium chloride aqueous solution, then dried with anhydrous magnesium sulfate. The dried chloroform extract was concentrated and was purified by a silica gel column chromatography (eluant: chloroform/methanol=50/1). The elute was recrystallized from chloroform-isopropyl ether to yield 0.5 g of 5-{2-[2,6-dimethyl-5-methoxycarbonyl-4-(3-nitrophenyl)-1,4-dihydropyridin-3-carboxy]ethoxy}-3,4-dihydrocarbostyril in the form of yellowish powdery crystals.

Melting point: 262°–263.5° C.

EXAMPLE 50

By a method similar to that described in Example 49, there were prepared compounds of Examples 2, 4–8, 11–14, 16, 24, 26–29, 32 and 33–48.

EXAMPLE 51

1.3 Grams of 6-{2-[2-(3-nitrobenzyliden)acetoacetoxy]ethoxy}-3,4-dihydrocarbostyril and 0.5 g of methyl 3-aminocrotonate were added to 10 ml of pyridine and the mixture was refluxed for 8 hours. The reaction mixture was concentrated, then the residue was extracted with chloroform, washed with a saturated aqueous solution of potassium hydrogensulfate and with a saturated aqueous solution of sodium chloride, and dried with anhydrous magnesium sulfate. The dried extract was concentrated and the residue was purified by a silica gel column chromatography (eluant: chloroform/methanol=100/1), then was recrystallized from chloroform-ether to yield 0.92 g of 6-{2-[2,6-dimethyl-5-methoxycarbonyl-4-(3-nitrophenyl)-1,4-dihydropyridin-3-carboxy]ethoxy}-3,4-dihydrocarbostyril in the form of light yellowish powdery crystals.

Melting point: 172.5°–174° C.

EXAMPLE 52

By a method similar to that described in Example 51, there were prepared compounds of Examples 1–25 and 27–48.

EXAMPLE 53

15 Grams of 5-{3-[2,6-dimethyl-5-methoxycarbonyl-4-(3-nitrophenyl)-1,4-dihydropyridin-3-carboxy]propoxy}-8-(2-tetrahydropyranoxy)-3,4-dihydrocarbostyril were added to a mixture of 100 ml of tetrahydrofuran and 30 ml of water, then 2 ml of 10%-hydrochloric acid were added to the mixture which was stirred at room temperature overnight. The reaction mixture was concentrated and the residue was extracted with chloroform, then the chloroform extract was washed with a saturated aqueous solution of sodium chloride, and with a saturated aqueous solution of sodium hydrogencarbonate, then dried with anhydrous magnesium sulfate, and the dried extract was concentrated. To the residue obtained was added ether and the insoluble matter formed was collected by filtration, then recrystallized from water-containing methanol to yield 8.9 g of 5-{3-[2,6-dimethyl-5-methoxycarbonyl-4-(3-nitrophenyl)-1,4-dihydropyridin-3-carboxy]propoxy}-8-hydroxy-3,4-dihydrocarbostyril in the form of yellowish prismatic crystals. Melting point: 193.5°–194° C.

EXAMPLE 54

2.7 Grams of 5-{3-[2,6-dimethyl-5-methoxycarbonyl-4-(3-nitrophenyl)-1,4-dihydropyridin-3-carboxy]propoxy}-8-hydroxy-3,4-dihydrocarbostyril, 0.7 g of potassium carbonate and 0.74 g propyl bromide were added to 30 ml of acetone and the whole mixture was refluxed for 3 hours. The reaction mixture was concentrated and the residue was extracted with chloroform, the extract was washed with 1N-sodium hydroxide aqueous solution, then the precipitate formed was removed by filtration. The organic layer was washed with a saturated sodium chloride aqueous solution, then dried with anhydrous magnesium sulfate and was concentrated. The residue obtained was purified by a silica gel column chromatography (eluant: chloroform/methanol=100/1), then the elute was concentrated and the residue was recrystallized from methanol to yield 0.8 g of 5-{3-[2,6-dimethyl-5-methoxy carbonyl-4-(3-nitrophenyl)-1,4-dihydropyridin-3-carboxy]propoxy}-8-propoxy-3,4-dihydrocarbostyril in the form of light yellowish prism-like crystals. Melting point: 150.5°–152.0° C.

EXAMPLE 55

By a method similar to that described in Example 54, there were prepared compounds of Examples 3, 9, 15 and 24.

EXAMPLE 56

3.2 Grams of 6-(4-acetoacetoxybutoxy)-3,4-dihydrocarbostyril, 1.5 g of 2-methylmercaptobenzaldehyde and 1.2 g of methyl 3-aminocrotonate were added to 20 ml of isopropanol, and the reaction mixture was refluxed for 8 hours under heating. The reaction mixture was then concentrated, and the residue obtained was purified by a silica gel column chromatography (eluant: chloroform/methanol=50/1). The elute was concentrated, and to the residue obtained was added 50%-water-containing methanol and with stirring at room temperature for 2 days to precipitate crude crystals. The crude crystals were recrystallized from water-containing methanol to yield 1.2 g of 6-{4-[2,6-dimethyl-5-methyl-5-methoxycarbonyl-4-(2-methylthiophenyl)-1,4-dihydropyridin-3-carboxy]butoxy}-3,4-dihydrocarbostyril in the form of light yellowish needle-like crystals.

Melting point: 90°–92° C.

EXAMPLE 57

3.0 Grams of methyl β,γ-epoxypropyl 2,6-dimethyl-4-(3-nitrophenyl)-1,4-dihydropyridin-3,5-dicarboxylate, 1.25 g of 6-hydroxy-3,4-dihydrocarbostyril and 1.1 g of potassium carbonate in 30 ml of dimethylformamide were heated at 100°–120° C. for 4 hours with stirring. Dimethylformamide was removed from the reaction mixture by distillation, then to the residue obtained was added water then the mixture was extracted with chloroform. The chloroform extract was washed with water, dried and the solvent was removed by distillation. The residue obtained was purified by a silica gel column chromatography (eluant: chloroform, next with chloroform/methanol=50/1), and the eluate was recrystallized from chloroform-isopropyl ether to yield 1.2 g of 6-{3-[2,6-dimethyl-5-methoxycarbonyl-4-(3-nitrophenyl)-1,4-dihydropyridin-3-carboxy]-2-hydropropoxy}-3,4-dihydrocarbostyril in the form of yellowish powdery crystals.

NMR δ (CDCl$_3$); 2.25 (3H, s), 2.29 (3H, s), 2.30–2.90 (4H, m), 3.53 (3H, s), 3.50–3.9 (2H, m), 3.90–4.30 (3H, m), 5.00 (1H, s), 6.50 (3H, bs), 6.70 (1H, bs), 7.00–8.00 (4H, m), 8.81 (1H, bs).

EXAMPLE 58

By a method similar to that described in Example 57, there was prepared the compound of Example 36, by using a suitable starting material.

EXAMPLE 59

To 3 ml of a pyridine solution containing 0.8 g of 6-{3-[2,6-dimethyl-5-methoxycarbonyl-4-(3-nitrophenyl)-1,4-dihydropyridin-3-carboxy]-2-hydroxypropoxy}-3,4-dihydrocarbostyril was added 0.3 ml of acetic anhydride and the mixture was stirred at room temperature overnight. Then water was added to the reaction mixture, and the mixture was extracted with ethyl acetate. The ethyl acetate extract was washed with water, dried, the solvent was removed by distillation, and the residue obtained was recrystallized from chloroform-isopropyl ether to yield 0.4 g of 6-{3-[2,6-dimethyl-5-methoxycarbonyl-4-(3-nitrophenyl)-1,4-dihydropyridin-3-carboxy]-2-acetoxypropoxy}-3,4-dihydrocarbostyril in the form of a yellowish powdery substance.

NMR δ (CDCl$_3$); 2.00 (3H, s), 2.27 (3H, s), 2.30 (3H, s), 2.50 (2H, t, J=7 Hz), 2.84 (2H, t, J=7 Hz), 3.89 (3H, s), 3.83 (2H, t, J=6 Hz), 4.23 (2H, t, J=5 Hz), 5.00 (1H, s), 5.10–5.30 (1H, m), 6.40–6.70 (3H, m), 6.70 (1H, bs), 7.10–8.00 (4H, m), 8.96 (1H, bs).

EXAMPLE 60

By a method similar to that described in Example 59, by using a suitable starting material, there was prepared a compound of Example 37.

EXAMPLE 61

In 20 ml of chloroform, 0.44 g of 1,5-diazabicyclo[5,4,0]undecene-5 (DBU) and 0.6 g of 4-(6-carbostyriloxybutyric acid were dissolved, then under an ice-cooled condition, 0.36 g of isobutyl chloroformate was added dropwise thereto. The reaction mixture was stirred at the same temperature for 2 hours, next 1 g of N-cyclohexylaminoethyl methyl 1,4-dihydro-2,6-dimethyl-4-(3-nitrophenyl)pyridin-3,5-dicarboxylate was added to the reaction mixture which was stirred at room temperature overnight. The precipitate formed was removed by filtration, the filtrate was washed with 5%-hydrochloric acid aqueous solution, 2%-sodium hydroxide aqueous solution, then with a saturated sodium chloride aqueous solution, and dried with anhydrous magnesium sulfate. The organic layer was concentrated, and the residue was purified by a silica gel column chromatography (eluant: chloroform/methanol=50/1), then the eluate was recrystallized from water-containing methanol to yield 0.4 g of N-{2-[1,4-dihydro-2,6-dimethyl-5-methoxycarbonyl-4-(3-nitrophenyl)-pyridin-3-carboxy]ethyl}-N-cyclohexyl-4-(6-carbostyriloxy)-butyramide in the form of yellowish powdery crystals.

| Elementary analysis: as C$_{37}$H$_{42}$H$_4$O$_9$ | | | |
| --- | --- | --- | --- |
|  | C | H | N |
| Calculated (%): | 64.71 | 6.16 | 8.16 |
| Found (%): | 64.35 | 6.12 | 8.06 |

Infrared absorption spectrum (KBr): As shown in FIG. 1.

Figure 2:
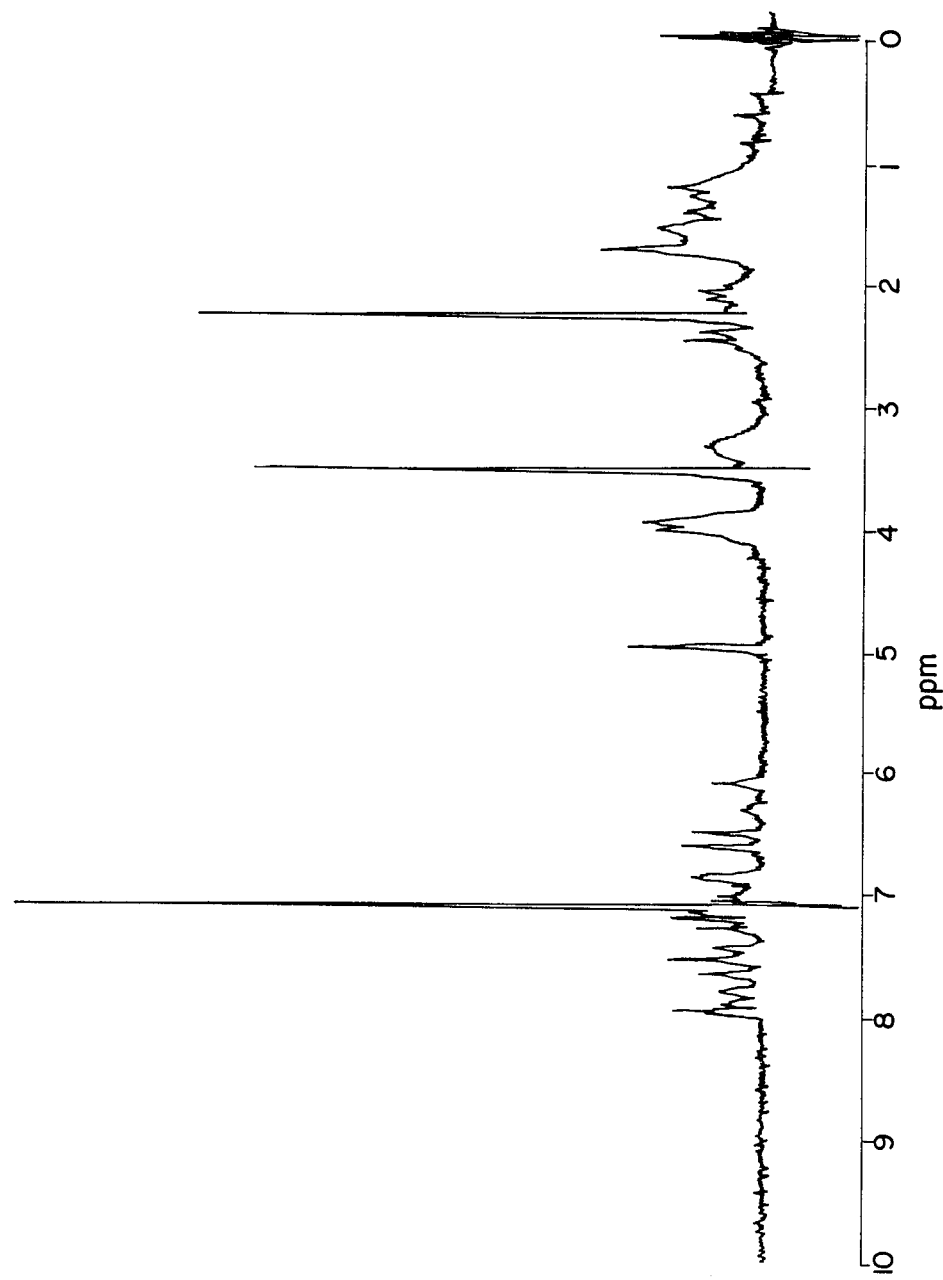
FIG. 2 is a nuclear magnetic resonance (NMR) spectrum of said compound.

NMR (90 MHz, CDCl$_3$, Zevo, Ref. TMS): As shown in FIG. 2.

EXAMPLES 62–66

By a method similar to that described in Exampel 61, there were prepared compounds of Examples 62–66 as follows:

EXAMPLE 62

N-{2-[1,4-Dihydro-2,6-dimethyl-5-methoxycarbonyl-4-(3-nitrophenyl)pyridin-3-carboxy]ethyl}-N-cyclohexyl-4-(3,4-dihydro-6-carbostyriloxy)butyramide.

Yellowish powdery crystals (from chloroformisopropyl ether).

| Elementary analysis for C$_{37}$H$_{44}$N$_4$O$_9$: | | | |
| --- | --- | --- | --- |
|  | C | H | N |
| Calculated (%): | 64.52 | 6.44 | 8.14 |

-continued

Elementary analysis for $C_{37}H_{44}N_4O_9$:

|  | C | H | N |
|---|---|---|---|
| Found (%): | 64.25 | 6.35 | 8.04 |

Figure 3:
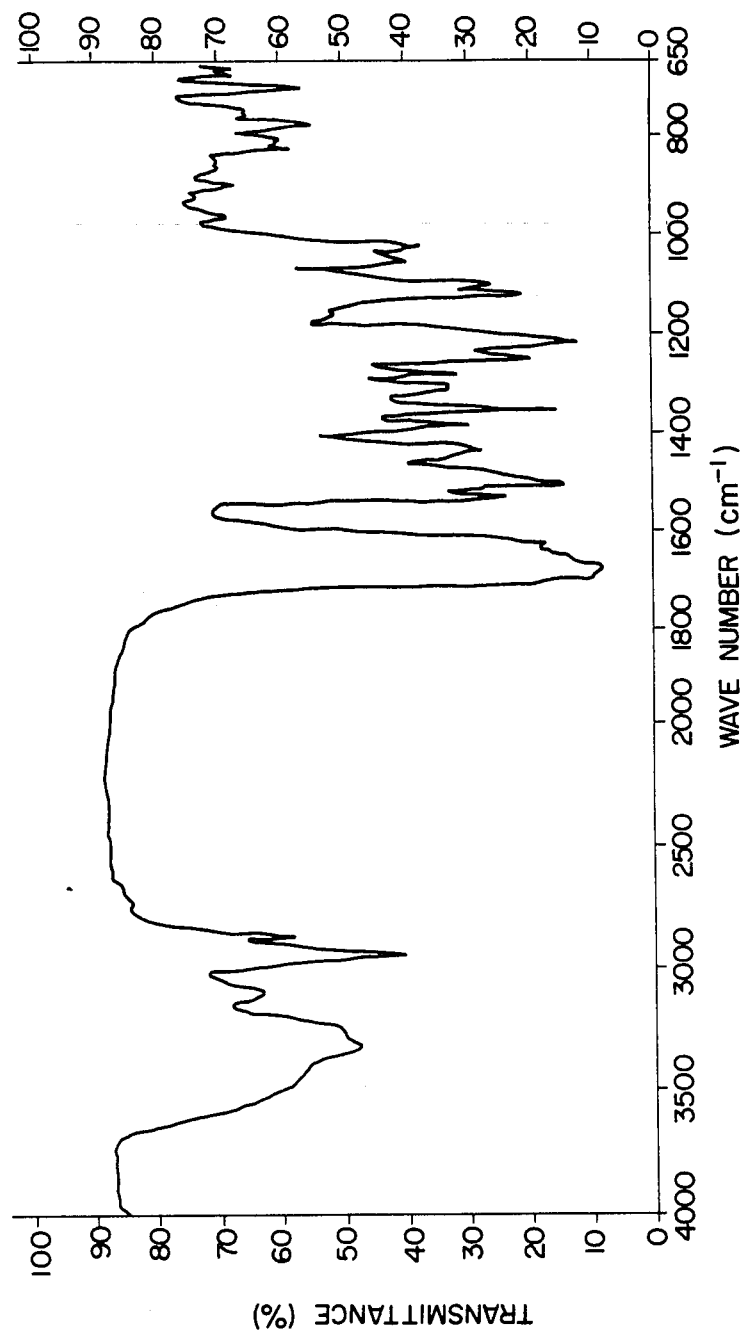
FIG. 3 is an infrared (IR) absorption spectrum of the compound prepared in Example 62.

Infrared absorption spectrum (KBr): As shown in FIG. 3.

Figure 4:
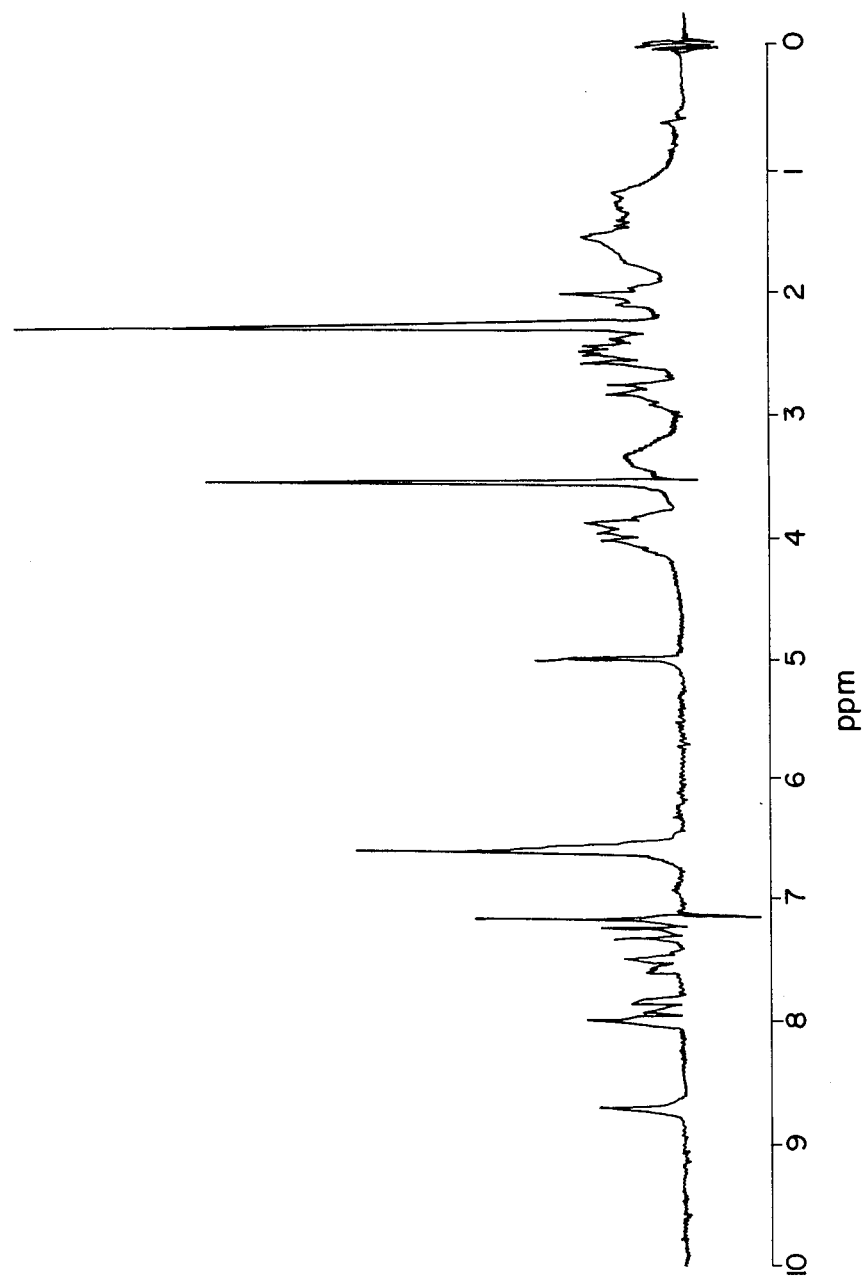
FIG. 4 is a nuclear magnetic resonance (NMR) spectrum of said compound.

NMR (90 MHz, CDCl$_3$, Zevo, Ref. TMS): As shown in FIG. 4.

EXAMPLE 63

N-{2-[1,4-Dihydro-2,6-dimethyl-5-methoxycarbonyl-4-(3-nitrophenyl)pyridin-3-carboxy]ethyl}-N-cyclohexyl-4-(5-carbostyriloxy)butyramide.

Yellowish powdery crystals (from chloroformisopropyl ether).

Elementary analysis for $C_{37}H_{42}N_4O_9$:

|  | C | H | N |
|---|---|---|---|
| Calculated (%): | 64.71 | 6.16 | 8.16 |
| Found (%): | 64.45 | 6.08 | 7.95 |

Figure 5:
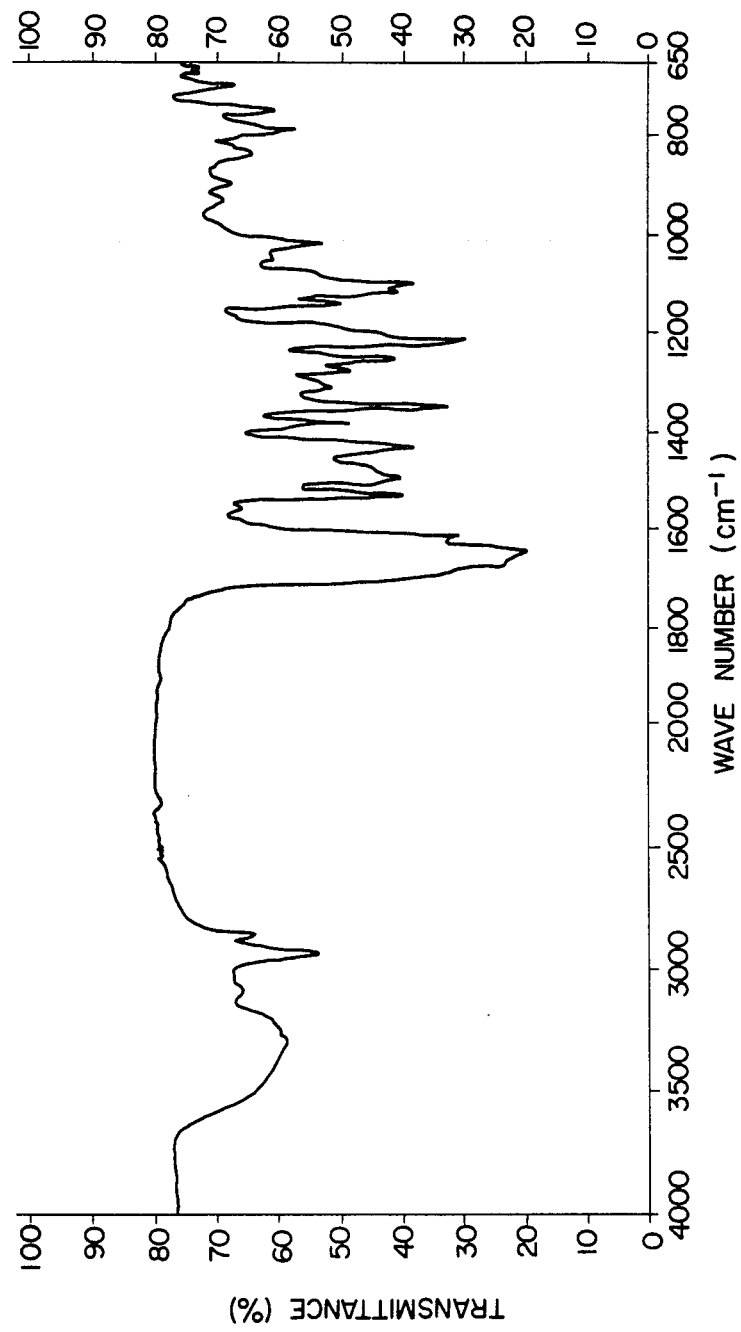
FIG. 5 is an infrared (IR) absorption spectrum of the compound prepared in Example 63.

Infrared absorption spectrum (KBr): As shown in FIG. 5.

Figure 6:
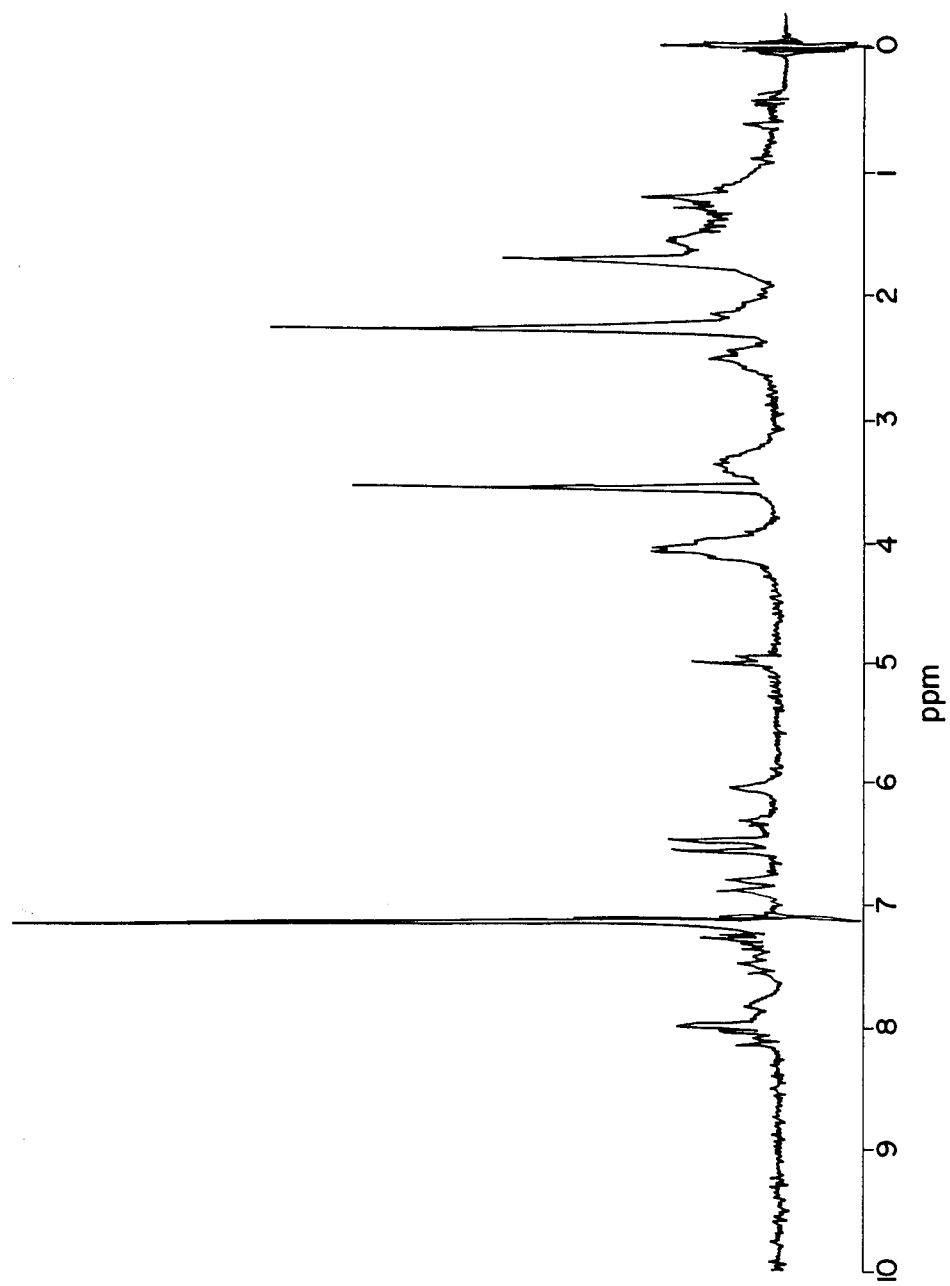
FIG. 6 is a nuclear magnetic resonance (NMR) spectrum of said compound.

NMR (90 MHz, CDCl$_3$, Zevo Ref. TMS): As shown in FIG. 6

EXAMPLE 64

N-{2-[1,4-Dihydro-2,6-dimethyl-5-methoxycarbonyl-4-(2-nitrophenyl)pyridin-3-carboxy]ethyl}-N-cyclohexyl-4-(6-carbostyriloxy)butyramide.

Yellowish powdery crystals (from chloroformisopropyl ether).

Elementary analysis for $C_{37}H_{42}N_4O_9$:

|  | C | H | N |
|---|---|---|---|
| Calculated (%): | 64.71 | 6.16 | 8.16 |
| Found (%): | 64.33 | 6.04 | 8.12 |

Figure 7:
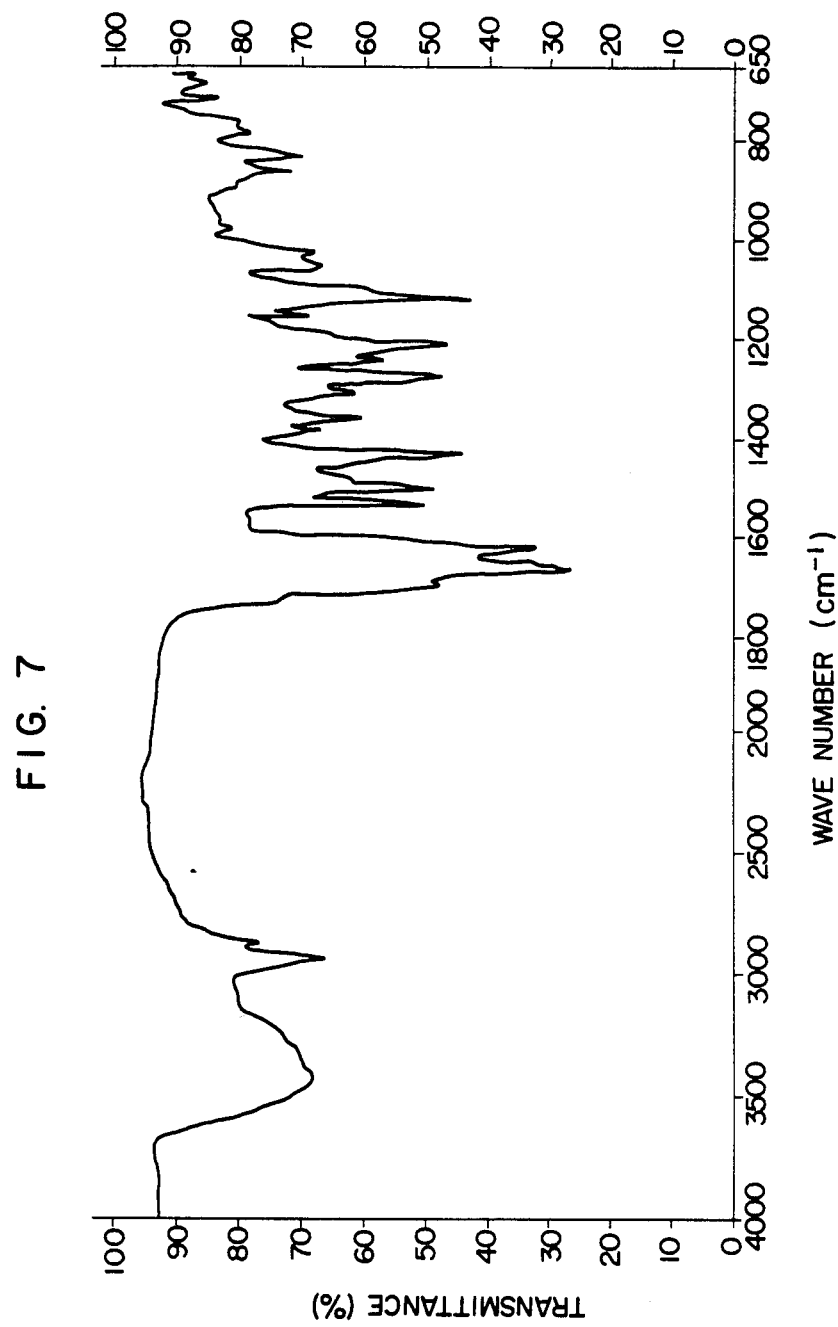
FIG. 7 is an infrared (IR) absorption spectrum of the compound prepared in Example 64.

Infrared absorption spectrum (KBr): As shown in FIG. 7

EXAMPLE 65

N-[2-(1,4-Dihydro-2,6-dimethyl-5-methoxycarbonyl-4-phenylpyridin-3-carboxy)ethyl]-N-cyclohexyl-4-(6-carbostyriloxy)butyramide.

Colorless powdery crystals (from chloroformisopropyl ether).

Elementary analysis for $C_{37}H_{43}N_3O_7$:

|  | C | H | N |
|---|---|---|---|
| Calculated (%): | 69.24 | 6.75 | 6.55 |
| Found (%): | 68.95 | 6.70 | 6.35 |

Figure 8:
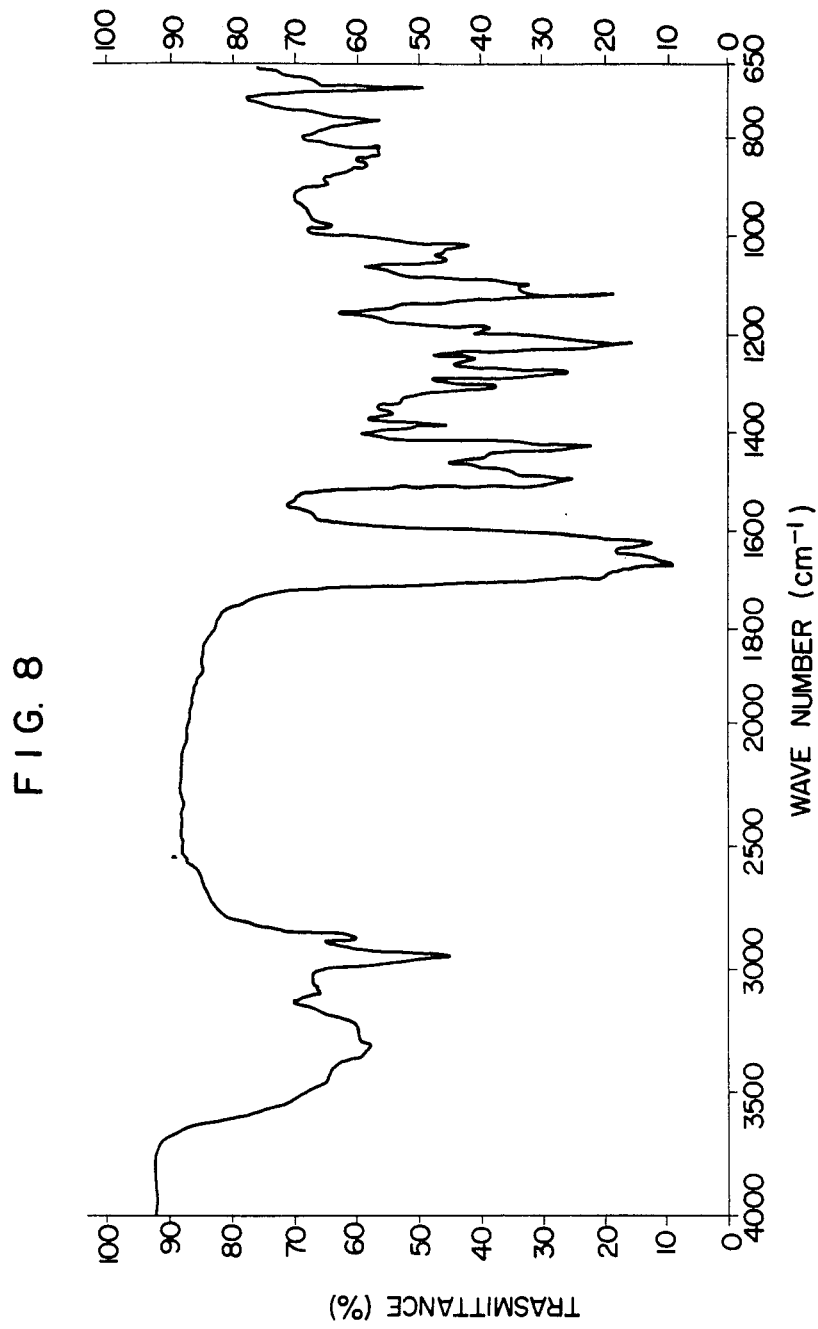
FIG. 8 is an infrared (IR) absorption spectrum of the compound prepared in Example 65.

Infrared absorption spectrum (KBr): As shown in FIG. 8.

Figure 9:
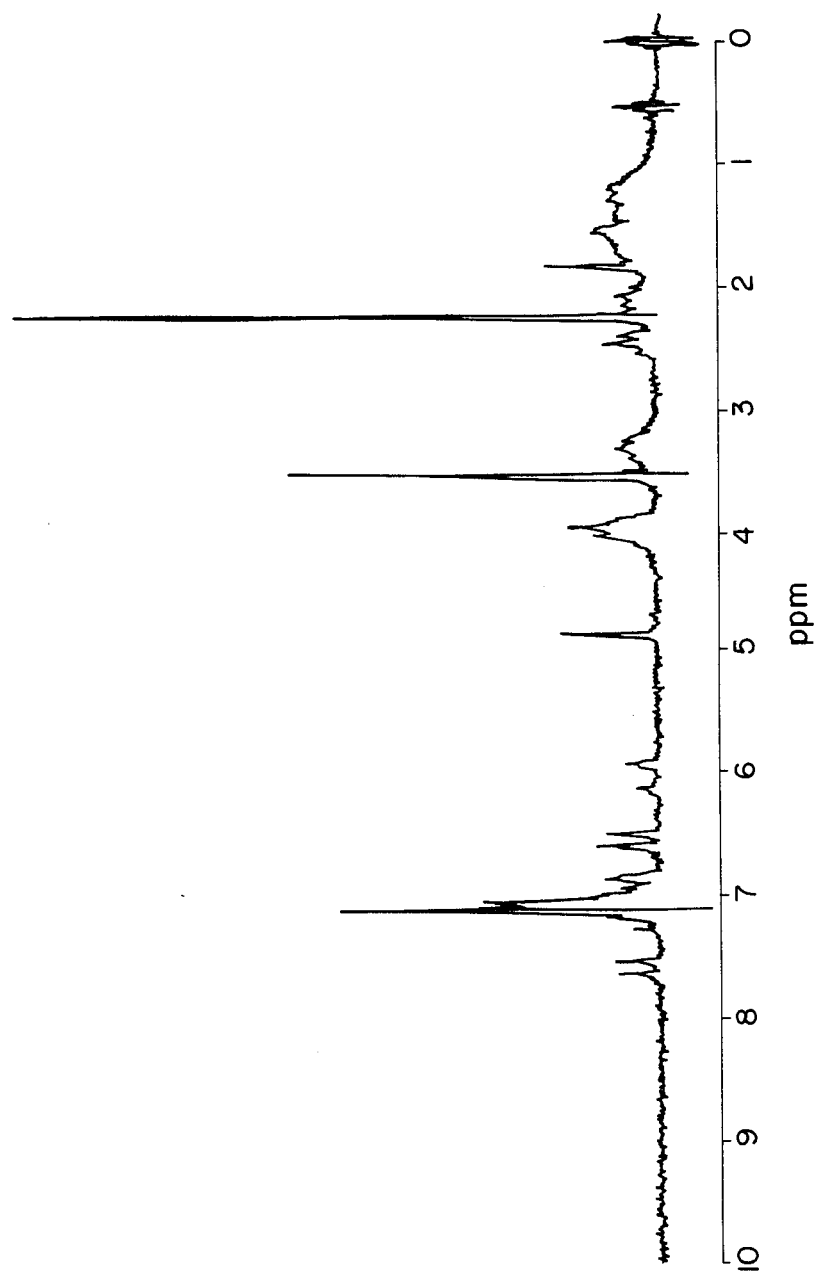
FIG. 9 is a nuclear magnetic resonance (NMR) spectrum of said compound.

NMR (90 MHz, CDCl$_3$, Zero Ref. TSM): As shown in FIG. 9.

EXAMPLE 66

N-[2-(1,4-Dihydro-2,6-dimethyl-5-methoxycarbonyl-4-phenylpyridin-3-carboxy)ethyl]-N-ethyl-4-(6-carbostyriloxy)butyramide.

Colorless powdery crystals (from chloroformisopropyl ether).

Elementary analysis for $C_{33}H_{37}N_3O_7$:

|  | C | H | N |
|---|---|---|---|
| Calculated (%): | 67.44 | 6.35 | 7.15 |
| Found (%): | 67.26 | 6.10 | 7.08 |

Figure 10:
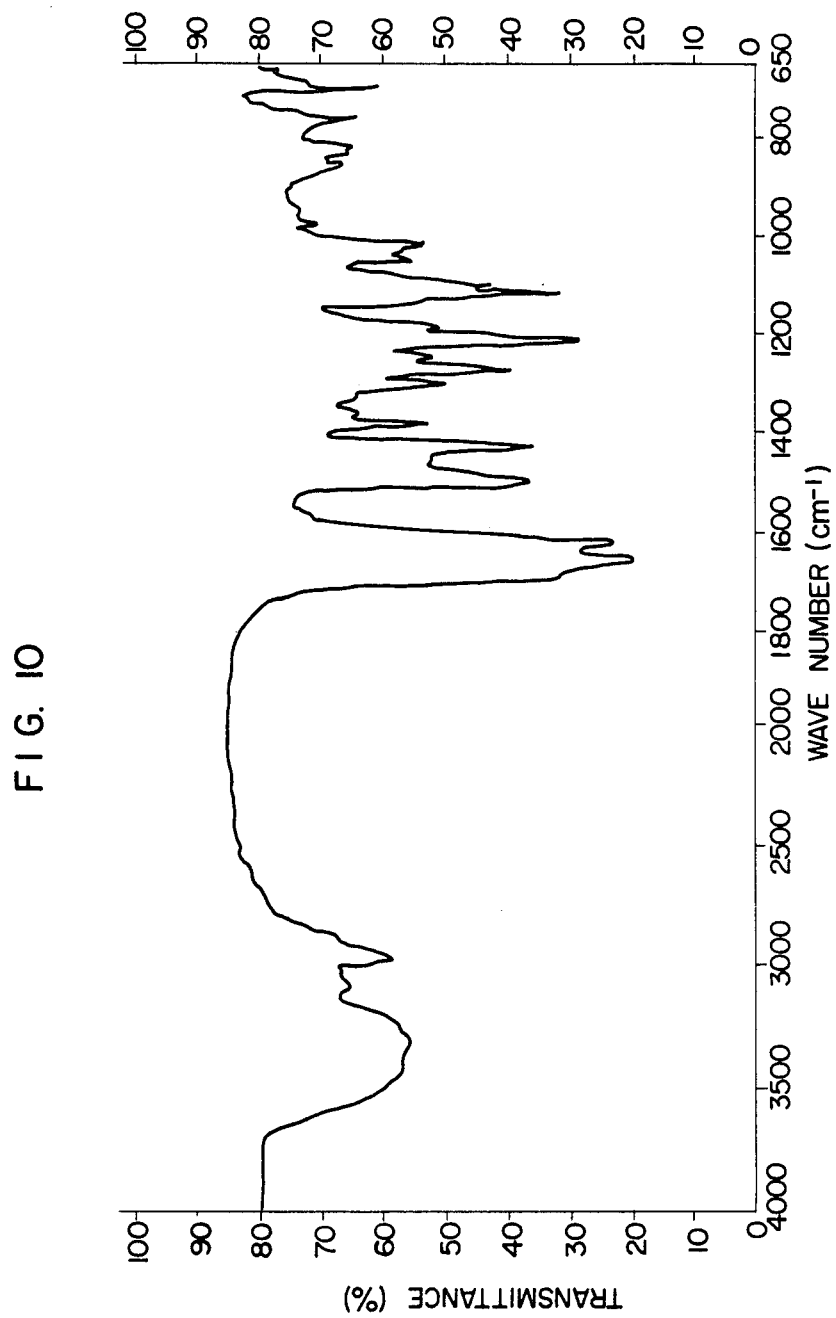
FIG. 10 is an infrared (IR) absorption spectrum of the compound prepared in Example 66.

Infrared absorption spectrum (KBr): As shown in FIG. 10.

Figure 11:
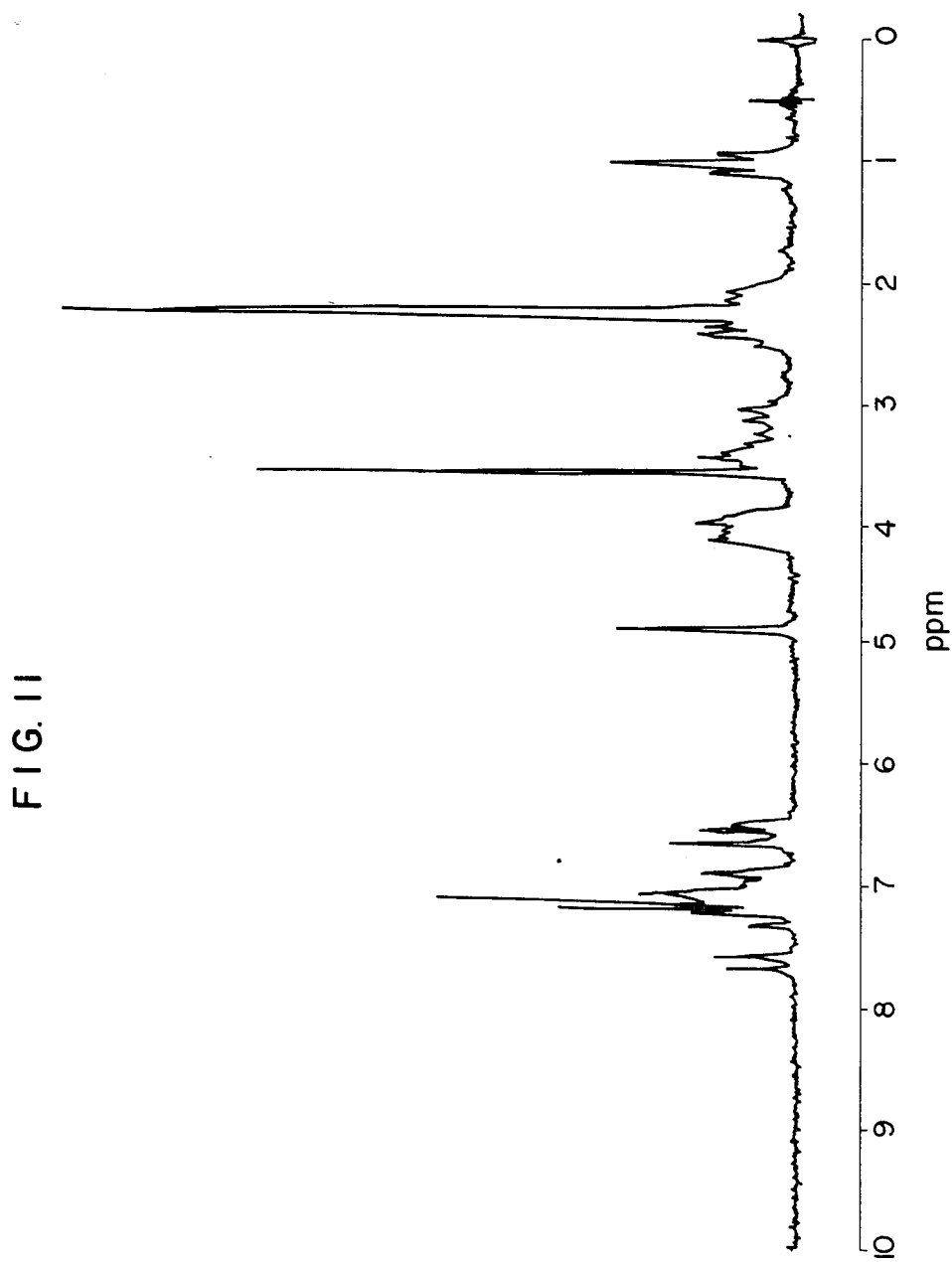
FIG. 11 is a nuclear magnetic resonance (NMR) spectrum of said compound.

NMR (90 MHz, CDCl$_3$, Zevo Ref. TMS): As shown in FIG. 11.

EXAMPLE 67

To 20 ml of dimethylformamide, were added 1.2 g of 4-(-3,4-dihydro-6-carbostyriloxy)butyric acid, 2.0 g of 2-cyclohexylaminoethyl methyl 1,4-dihydro-2,6-dimethyl-4-(3-nitrophenyl)pyridin-3,5-dicarboxylate and 1.1 g of dicyclohexylcarbodiimide, then the mixture was stirred at 60° C. for 4 hours. After cooling, the precipitates were removed by filtration and the filtrate was concentrated, then the residue was purified by a silica gel column chromatography (eluant: chloroform/methanol=50/1), and the eluate was recrystallized from chloroform-isopropyl ether to yield 0.4 g of N-{2-[1,4-dihydro-2,6-dimethyl-5-methoxycarbonyl-4-(3-nitrophenyl)pyridin-3-carboxy]ethyl}-N-cyclohexyl-4-(3,4-dihydro-6-carbostyriloxy)butyramide. This substance shows the same physical properties of those of the compound prepared in Example 2.

EXAMPLE 68

By a method similar to that described in Example 67, there were prepared compounds of Examples 61 and 63–66.

EXAMPLE 69

1.6 Grams of 6-hydroxycarbostyril and 1.5 g of potassium carbonate were added to 30 ml of dimethylformamide and the mixture was heated at 80°–90° C.; then to this reaction mixture was added dropwise a dimethylformamide solution containing 6 g of 2-N-(4-chlorobutyryl)-N-cyclohexylaminoethyl methyl 1,4-dihydro-2,6-dimethyl-4-(3-nitrophenyl)pyridine 3,5-dicarboxylate. Then the reaction mixture was stirred for 6 hours at the same temperature. The reaction mixture was concentrated, then the residue obtained was extracted with chloroform, and the chloroform extract was washed with water, 0.5N-sodium hydroxide, 5%-hydrochloric acid and a saturated sodium chloride aqueous solution, then dried with anhydrous magnesium sulfate. The dried chloroform extract was concentrated, then the residue was purified by a silica gen column chromatography (eluant: chloroform/methanol=50/1), and recrystallized from a water-containing methanol to yield 0.3 g of N-{2-[1,4-dihydro-2,6-dimethyl-5-methoxycarbonyl-4-(3-nitrophenyl)pyridin-3-carboxy]ethyl}-N-cyclohexyl-4-(6-carbostryriloxy)-butyramide. This substance shows physical properties the same as those of the compound of Example 61.

EXAMPLE 70

By a method similar to that described in Example 69, there were prepared compounds of Examples 62–66.

Example 71

3.0 Grams of 1,4-dihydro-2,6-dimethyl-5-methoxycarbonyl-4-(2-nitrophenyl)pyridin-3-carboxylic acid, 3.8 g of N-(2-hydroxyethyl)-N-cyclohexyl-4-(6-carbostyriloxy)butyramide and 2.1 g of dicyclohexylcarbodiimide were added to 30 ml of dimethylformamide, then the mixture was heated at 60° C. for 2 hours. Then the reaction mixture was cooled, and filtered, the filtrate obtained was concentrated, and the residue obtained was purified by a silica gel column chromatography (eluant: chloroform/methanol=50/1). Recrystallization from chloroform-isopropyl ether yielded 0.3 g of N-{2-[1,4-dihydro-2,6-dimethyl-5-methoxycarbonyl-4-(2-nitrophenyl)pyridin-3-carboxy]ethyl}-N-cyclohexyl-4-(6-carbostyriloxy)butyramide. This substance shows the same physical properties as those of the compound of Example 64.

EXAMPLE 72

A method similar to that described in Example 71, there were prepared compounds of Examples 61–63, 65 and 66.

EXAMPLE 73

To 20 ml of methanol, were added 3 g of N-{2-[2-(3-nitrobenzyliden)acetoactoxy]ethyl}-N-cyclohexyl-4-(6-carbostyriloxy)butyramide and 0.6 g of methyl 3-aminocrotonate, then the mixture was refluxed for 15 hours. The reaction mixture was concentrated, and the residue obtained was purified by a silica gel column chromatography (eluant: chloroform/methanol=50/1). The elute was recrystallized from a water-containing methanol to yield 0.3 g of N-{2-[1,4-dihydro-2,6-dimethyl-5-methoxycarbonyl-4-(3-nitrophenyl)pyridin-3-carboxy]ethyl}-N-cyclohexyl-4-(6-carbostyriloxy)butyramide in the form of yellowish powdery crystals. This product shows physical properties the same as those of the compound prepared in Example 61.

EXAMPLE 74

By a method similar to that described in Example 73, there were prepared compounds of Examples 62 and 63.

What is claimed is:

1. A carbostyril derivative represented by the formula

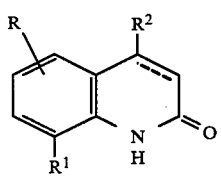

(1)

wherein R is a hydrogen atom or a group of the formula

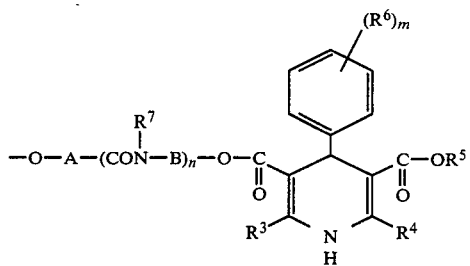

wherein $R^3$, $R^4$ and $R^5$ are each a lower alkyl group; A is a lower alkylene group which may have a hydroxyl group or a lower alkanoyloxy group as a substituent; $R^6$ is a nitro group, a lower alkyl group which may have a halogen atom as a substituent, a halogen atom, a lower alkoxy group, a lower alkylthio group, a lower alkoxycarbonyl group; $R^7$ is a lower alkyl group or a cycloalkyl group having 3 to 8 carbon atoms; B is a lower alkylene group; n is 0 or 1; and m is 0 or an integer of 1, 2 or 3, with the proviso that when $R^6$ is a nitro group, m is 1; $R^1$ is a hydrogen atom, a hydroxyl group, a lower alkoxy group, a lower alkenyloxy group, a lower alkynyloxy group, a 2-tetrahydropyranyloxy group or a group of the formula

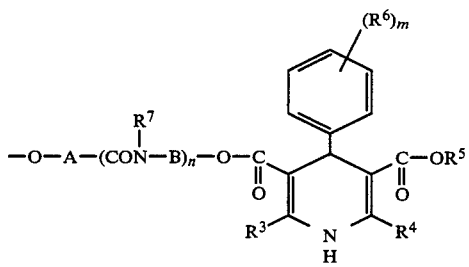

wherein $R^3$, $R^4$, $R^5$, $R^6$, $R^7$, A, B, m and n are the same as defined above $R^2$ is a hydrogen atom, a lower alkyl group or a group of the formula

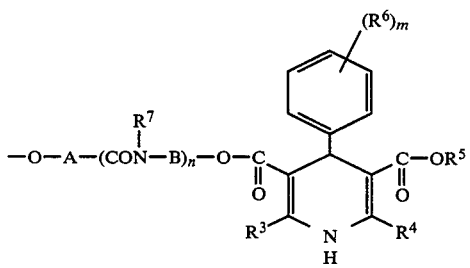

wherein $R^3$, $R^4$, $R^5$, $R^6$, $R^7$, A, B, m and n are the same as defined above; provided that, among R, $R^1$ and $R^2$, only one is a group of the formula

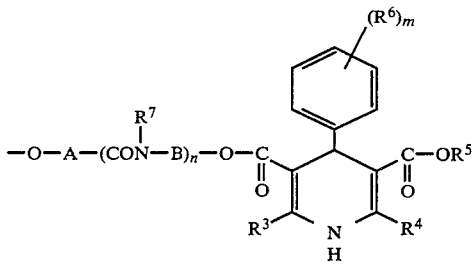

wherein $R^3$, $R^4$, $R^5$, $R^6$, $R^7$, A, B, m and n are the same as defined above; and the carbon-carbon bond between 3- and 4-positions in the carbostyril skeleton is a single or double bond, or a pharmaceutically acceptable acid addition salt thereof.

2. The carbostyril derivative as claimed in claim 1, wherein n is 0.

3. The carbostyril derivative as claimed in claim 1, wherein n is 1.

4. The carbostyril derivative as claimed in claim 2, wherein $R^1$ is a hydrogen atom and $R^2$ is a hydrogen atom.

5. The carbostyril derivative as claimed in claim 2, wherein $R^1$ is a hydrogen atom and $R^2$ is a lower alkyl group.

6. The carbostyril derivative as claimed in claim 2, wherein $R^1$ is a hydroxyl group, a lower alkoxy group, a lower alkenyloxy group, a lower alkynyloxy group or a 2-tetrahydropyranyloxy group and $R^2$ is a hydrogen atom or a lower alkyl group.

7. The carbostyril derivative as claimed in claim 2, wherein $R^1$ is a group of the formula,

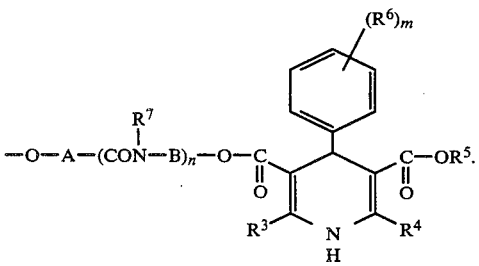

8. The carbostyril derivative as claimed in claim 2, wherein $R^2$ is a group of the formula,

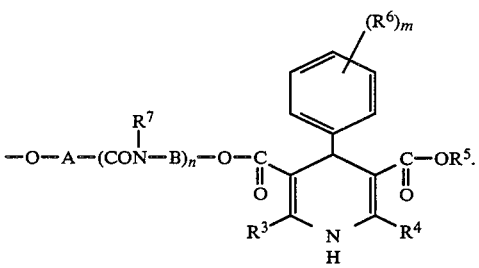

9. The carbostyril derivative as claimed in claim 3, wherein $R^1$ is a hydrogen atom, $R^2$ is a hydrogen atom, $R^6$ is a nitro group or a lower alkyl group which may have a halogen atom as a substituent.

10. The carbostyril derivative as claimed in claim 4, wherein $R^6$ is a nitro group or a lower alkyl group which may have a halogen atom as a substituent.

11. The carbostyril derivative as claimed in claim 4, wherein $R^6$ is a halogen atom or a lower alkylthio group.

12. The carbostyril derivative as claimed in claim 4, wherein $R^6$ is a lower alkoxy group or a lower alkoxycarbonyl group.

13. The carbostyril derivative as claimed in claim 10, 11 or 12, wherein the substituted position of the side-chain of the formula,

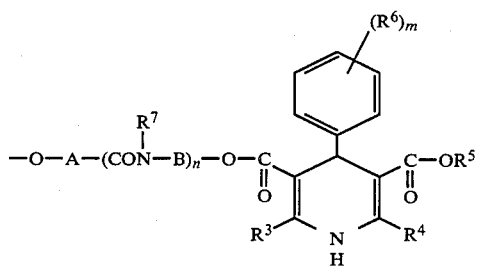

is 5-position in the carbostyril skeleton.

14. The carbostyril derivative as claimed in claim 10, 11 or 12, wherein the substituted position of the side-chain of the formula,

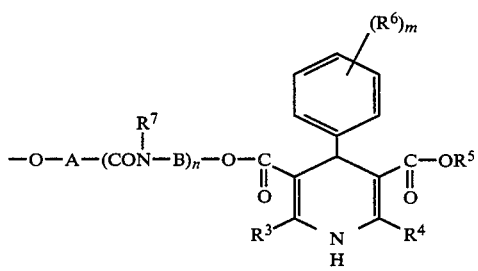

is 6-position in the carbosryril skeleton.

15. The carbostyril derivative as claimed in claim 5 or 6, wherein $R^6$ is a nitro group or a lower alkyl group which may have a halogen atom as a substituent, the substituted position of the side-chain of the formula,

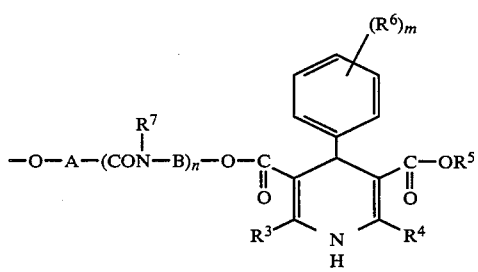

is 5- or 6-position in the carbostyril skeleton.

16. The carbostyril derivative as claimed in claim 3, wherein $R^1$ and $R^2$ are each a hydrogen atom, and $R^6$ is a nitro group or a lower alkyl group which may have a halogen atom as a substituent.

17. The carbostyril derivative as claimed in claim 16, wherein the substituted position of the side-chain of the formula,

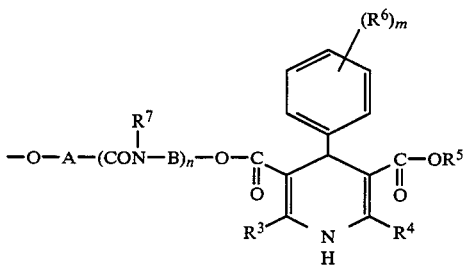

is 5- or 6-position in the carbostyril skeleton.

18. 6-{4-[2,6-Dimethyl-5-methoxycarbonyl-4-(2-nitrophenyl)-1,4-dihydropyridin-3-carboxy]butoxy}-3,4-dihydrocarbostyril.

19. 6-{4-[2,6-Dimethyl-5-methoxycarbonyl-4-(2-nitrophenyl)-1,4-dihydropyridin-3-carboxy]butoxy}-carbostyril.

20. 6-{4-[2,6-Dimethyl-5-methoxycarbonyl-4-(2-trifluoromethylphenyl)-1,4-dihydropyridin-3-carboxy]butoxy}-3,4-dihydrocarbostyril.

21. 6-{4-[2,6-Dimethyl-5-methoxycarbonyl-4-(2-trifluoromethylphenyl)-1,4-dihydropyridin-3-carboxy]butoxy}carbostyril.

22. 6-{3-[2,6-Dimethyl-5-methoxycarbonyl-4-(2-trifluoromethylphenyl)-1,4-dihydropyridin-3-carboxy]propoxy}-3,4-dihydrocarbostyril.

23. 6-{3-[2,6-Dimethyl-5-methoxycarbonyl-4-(2-trifluoromethylphenyl)-1,4-dihydropyridin-3-carboxy]propoxy}carbostyril.

24. 6-{3-[2,6-Dimethyl-5-methoxycarbonyl-4-(2-nitrophenyl)-1,4-dihydropyridin-3-carboxy]propoxy}-3,4-dihydrocarbostyril.

25. 6-{3-[2,6-Dimethyl-5-methoxycarbonyl-4-(2-nitrophenyl)-1,4-dihydropyridin-3-carboxy]propoxy}carbostyril.

26. A pharmaceutical composition for inhibiting platelet aggregation containing a pharmaceutically effective amount of a carbostyril derivative as claimed in claim 1 or a pharmaceutically acceptable acid addition salt thereof as the active ingredient.

* * * * *